(12) United States Patent
Wilson et al.

(10) Patent No.: US 9,946,839 B1
(45) Date of Patent: Apr. 17, 2018

(54) SEARCH ENGINE SYSTEMS FOR MATCHING MEDICAL PROVIDERS AND PATIENTS

(71) Applicant: MD Insider, Inc., Santa Monica, CA (US)

(72) Inventors: Eric Wilson, Los Angeles, CA (US); Kingshuk Chatterjee, Los Angeles, CA (US); David Norris, Malibu, CA (US)

(*) Notice: Subject to any disclaimer, the term of this patent is extended or adjusted under 35 U.S.C. 154(b) by 0 days.

(21) Appl. No.: 15/274,173

(22) Filed: Sep. 23, 2016

Related U.S. Application Data

(63) Continuation-in-part of application No. 14/482,921, filed on Sep. 10, 2014.

(60) Provisional application No. 62/222,329, filed on Sep. 23, 2015, provisional application No. 61/876,105, filed on Sep. 10, 2013.

(51) Int. Cl.
  *G06F 19/00* (2018.01)
  *G06F 17/30* (2006.01)

(52) U.S. Cl.
  CPC ........ *G06F 19/324* (2013.01); *G06F 17/3087* (2013.01); *G06F 17/30867* (2013.01)

(58) Field of Classification Search
  CPC ..... G06Q 10/1095; G06Q 50/22; G06Q 50/24
  See application file for complete search history.

(56) References Cited

U.S. PATENT DOCUMENTS

| | | | |
|---|---|---|---|
| 2008/0133290 A1* | 6/2008 | Siegrist | G06Q 50/22 705/2 |
| 2008/0215370 A1* | 9/2008 | Dent | G06F 19/3487 705/3 |
| 2012/0053963 A1* | 3/2012 | Seymour | G06Q 50/24 705/3 |

* cited by examiner

*Primary Examiner* — Maroun P Kanaan
(74) *Attorney, Agent, or Firm* — Baker Botts L.L.P.

(57) ABSTRACT

In one embodiment, a matching-engine system receives from a user a search query with a location of the user and a user-specified symptom or treatment. The matching-engine system determines a base-concept of a medical diagnosis or medical procedure based on the search query. The matching-engine system may identify a set of physicians to be recommended to the user based on factors relevant to the base-concept such as readmission rate, infection rate, average length-of-stay, relative invasiveness, and healthcare facility ratings. The matching-engine system may send a search-results page to the user listing the recommended physicians.

18 Claims, 32 Drawing Sheets

PERFORMANCE DATA

| | # of Proced. | Experience vs Peers | Cost vs Peers | Duration of Care | DISTANCE | SPECIALIZATION AND COMMON PROCEDURES |
|---|---|---|---|---|---|---|
| Benjamin F. Pierce, MD | 75 | MOST | $ | 33 | 7.2 miles | Sports medicine, orthopedic surgery, knee arthroscopy, rotatory cuff surgery |
| Camille Saroyan, MD, PhD | 65 | AVG | $$$ | 44 | 18 miles | Sports medicine, orthopedic surgery, knee arthroscopy, rotatory cuff surgery |
| Tony Gates, MD, PhD | 56 | MORE | $$ | 32 | 2.3 miles | Sports medicine, orthopedic surgery, knee arthroscopy, rotatory cuff surgery |
| Elliot Reid, MD | 31 | MORE | $ | 52 | 6.6 miles | Sports medicine, orthopedic surgery, knee arthroscopy, rotatory cuff surgery |
| Henry Jones, Jr., MD | 17 | AVG | $$$ | 77 | 24 miles | Sports medicine, orthopedic surgery, knee arthroscopy, rotatory cuff surgery |
| Wellington Yueh, MD | 15 | MOST | $$ | 50 | 5.7 miles | Sports medicine, orthopedic surgery, knee arthroscopy, rotatory cuff surgery |
| Nick S. Riviera, MD | 7 | LESS | $ | 75 | 0.2 miles | Sports medicine, orthopedic surgery, knee arthroscopy, rotatory cuff surgery |

*FIG. 10D*

ACME HEALTH — DOCTOR FINDER — SAM HAUFFEN

[ ANTERIOR CRUCIATE LIGAMENT (ACL) REPAIR [x] 🔍 ]

▽ FILTERS

AFFILIATION
- ● ALL (22)
- ○ CENTER OF EXCELLENCE (6)
- ○ STAFF (11)
- ○ NETWORK (22)

AVAILABILITY IN
- ● ALL (22)
- ○ 1 WEEK (4)
- ○ 2 WEEKS (13)
- ○ 1 MONTH (6)

HEALTH COVERAGE
- AETNA ▼
- AETNA CHOICE POS ▼

SEX
- ALL (22) ▼

LANGUAGE
- ENGLISH (22) ▼

YEARS IN PRACTICE
- ● ALL (22)
- ○ 5 YEARS (5)
- ○ 10 YEARS (12)
- ○ 20+ YEARS (6)

MD INSIDER

| SCORE ▽ | DOCTOR NAME | ACL TEAR REPAIR | AVAILABILITY | DISTANCE | COMPARE |
|---|---|---|---|---|---|
| 97 | STEPHAN V. YACOUBIAN, MD — ORTHOPEDIC SURGERY — CENTER FOR ORTHPEDICS | 137 | BEYOND A MONTH | 13.5 MILES | ☐ |
| 93 | BRADLEY M. THOMAS — SPORTS MEDICINE | 113 | ⊘ | 17.3 MILES | ☐ |
| 90 | HEATHER M. GILLESPIE, MD — ORTHOPEDICS | 110 | THIS WEEK | 1.1 MILES | ☐ |
| 85 | STEPHAN L. NUCCION, MD — SPORTS MEDICINE — CENTER FOR SPORTS MEDICINE | 107 | THIS WEEK | 17.3 MILES | ☐ |
| 84 | BERT R. MANDELBAUM, MD — ORTHOPEDIC SURGERY | 103 | THIS WEEK | 1.1 MILES | ☐ |
| 77 | DAVID R. MCALLISTER, MD — SPORTS MEDICINE | 98 | THIS WEEK | 13.2 MILES | ☐ |
| 72 | GARY Y. CHEN, MD — ORTHOPEDIC SURGERY | 45 | THIS WEEK | 13.2 MILES | ☐ |
| 70 | KIUMARS ARFI, MD — ORTHOPEDIC SURGERY | 43 | THIS WEEK | 18.1 MILES | ☐ |

SEARCH ENGINE SYSTEMS FOR MATCHING MEDICAL PROVIDERS AND PATIENTS

PRIORITY

This application claims the benefit, under 35 U.S.C. § 119(e), of U.S. Provisional Patent Application No. 62/222,329, filed 23 Sep. 2015, which is incorporated herein by reference. This application is also a continuation-in-part under 35 U.S.C. § 120 of U.S. patent application Ser. No. 14/482,921, filed 10 Sep. 2014, which claims the benefit, under 35 U.S.C. § 119(e), of U.S. Provisional Patent Application No. 61/876,105, filed 10 Sep. 2013, each of which is incorporated herein by reference.

TECHNICAL FIELD

This disclosure generally relates to search engines, and in particular, search engines for healthcare providers.

BACKGROUND

Users seeking medical care or treatment may wish to select a particular physician or health-care provider to visit to receive the care or treatment. Factors that may be considered when trying to select a particular provider may include costs, location, specialty, the provider's experience, etc. Currently, information about health-care providers is available via user-generated reviews on review websites. A user seeking a particular type of health-care provider or a specific medical treatment may be able to search the review websites for physicians in the particular type or performing the specific treatment. However, user-generated reviews are highly subjective, and may have incomplete information about a particular provider, or incomplete information about the available providers within a given geographic area.

Some users may have health insurance through their employer. The employer may maintain an administrator responsible for overseeing the employee health-care plan. The employer-administrator may set policy measures regarding which health-care providers should be visited by the employees on the health-care plan.

BRIEF DESCRIPTION OF THE DRAWINGS

FIG. 10A-10E illustrate example embodiments of a user interface for presenting recommended physicians to a user of a matching engine system.

FIG. 19 illustrates an example web interface showing a set of search results corresponding to a search query.

DESCRIPTION OF EXAMPLE EMBODIMENTS

System Overview

Figure 1:
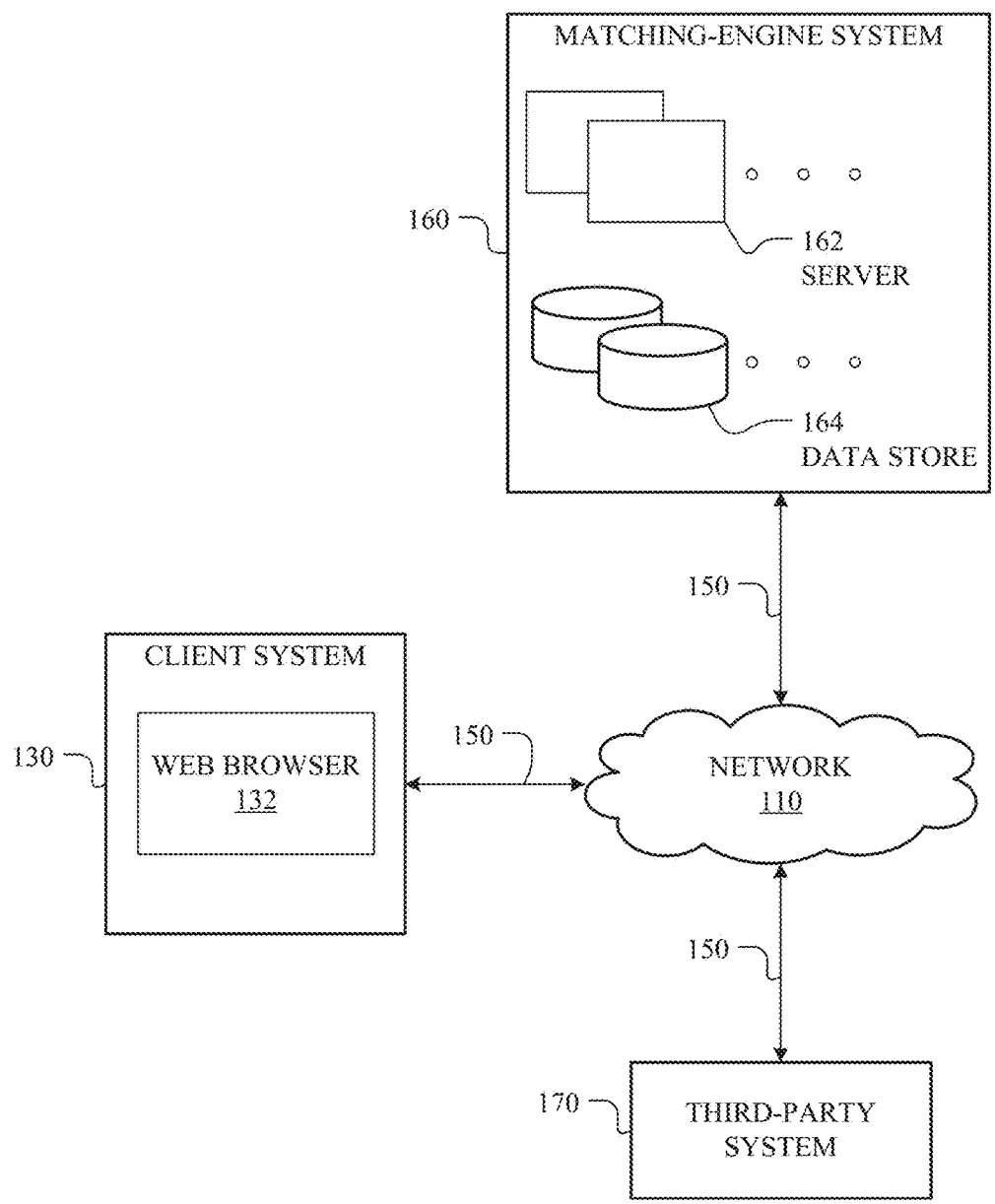
FIG. 1 illustrates an example network environment associated with a matching-engine system.

FIG. 1 illustrates an example network environment 100 associated with a matching-engine system. Network environment 100 includes a client system 130, a matching-engine system 160, and a third-party system 170 connected to each other by a network 110. Although FIG. 1 illustrates a particular arrangement of client system 130, matching-engine system 160, third-party system 170, and network 110, this disclosure contemplates any suitable arrangement of client system 130, matching-engine system 160, third-party system 170, and network 110. As an example and not by way of limitation, two or more of client system 130, matching-engine system 160, and third-party system 170 may be connected to each other directly, bypassing network 110. As another example, two or more of client system 130, matching-engine system 160, and third-party system 170 may be physically or logically co-located with each other in whole or in part. Moreover, although FIG. 1 illustrates a particular number of client systems 130, matching-engine systems 160, third-party systems 170, and networks 110, this disclosure contemplates any suitable number of client systems 130, matching-engine systems 160, third-party systems 170, and networks 110. As an example and not by way of limitation, network environment 100 may include multiple client system 130, matching-engine systems 160, third-party systems 170, and networks 110.

This disclosure contemplates any suitable network 110. As an example and not by way of limitation, one or more portions of network 110 may include an ad hoc network, an intranet, an extranet, a virtual private network (VPN), a local area network (LAN), a wireless LAN (WLAN), a wide area network (WAN), a wireless WAN (WWAN), a metropolitan area network (MAN), a portion of the Internet, a portion of the Public Switched Telephone Network (PSTN), a cellular telephone network, or a combination of two or more of these. Network 110 may include one or more networks 110.

Links 150 may connect client system 130, matching-engine system 160, and third-party system 170 to communication network 110 or to each other. This disclosure contemplates any suitable links 150. In particular embodiments, one or more links 150 include one or more wireline (such as for example Digital Subscriber Line (DSL) or Data Over Cable Service Interface Specification (DOC SIS)), wireless (such as for example Wi-Fi or Worldwide Interoperability for Microwave Access (WiMAX)), or optical (such as for example Synchronous Optical Network (SONET) or Synchronous Digital Hierarchy (SDH)) links. In particular embodiments, one or more links 150 each include an ad hoc network, an intranet, an extranet, a VPN, a LAN, a WLAN, a WAN, a WWAN, a MAN, a portion of the Internet, a portion of the PSTN, a cellular technology-based network, a satellite communications technology-based network, another link 150, or a combination of two or more such links 150. Links 150 need not necessarily be the same throughout network environment 100. One or more first links 150 may differ in one or more respects from one or more second links 150.

In particular embodiments, client system 130 may be an electronic device including hardware, software, or embedded logic components or a combination of two or more such components and capable of carrying out the appropriate functionalities implemented or supported by client system 130. As an example and not by way of limitation, a client system 130 may include a computer system such as a desktop computer, notebook or laptop computer, netbook, a tablet computer, e-book reader, GPS device, camera, personal digital assistant (PDA), handheld electronic device, cellular telephone, smartphone, other suitable electronic device, or any suitable combination thereof. This disclosure contemplates any suitable client systems 130. A client system 130 may enable a network user at client system 130 to access network 110. A client system 130 may enable its user to communicate with other users at other client systems 130.

In particular embodiments, client system 130 may include a web browser 132, such as MICROSOFT INTERNET EXPLORER, GOOGLE CHROME or MOZILLA FIREFOX, and may have one or more add-ons, plug-ins, or other extensions, such as TOOLBAR or YAHOO TOOLBAR. A user at client system 130 may enter a Uniform Resource Locator (URL) or other address directing the web browser 132 to a particular server (such as server 162, or a server associated with a third-party system 170), and the web browser 132 may generate a Hyper Text Transfer Protocol (HTTP) request and communicate the HTTP request to server. The server may accept the HTTP request and communicate to client system 130 one or more Hyper Text Markup Language (HTML) files responsive to the HTTP request. Client system 130 may render a webpage based on the HTML files from the server for presentation to the user. This disclosure contemplates any suitable webpage files. As an example and not by way of limitation, webpages may render from HTML files, Extensible Hyper Text Markup Language (XHTML) files, or Extensible Markup Language (XML) files, according to particular needs. Such pages may also execute scripts such as, for example and without limitation, those written in JAVASCRIPT, JAVA, MICROSOFT SILVERLIGHT, combinations of markup language and scripts such as AJAX (Asynchronous JAVASCRIPT and XML), and the like. Herein, reference to a webpage encompasses one or more corresponding webpage files (which a browser may use to render the webpage) and vice versa, where appropriate.

In particular embodiments, matching-engine system 160 may be a network-addressable computing system that can host an online healthcare provider search engine. Matching-engine system 160 may generate, store, receive, and send patient data, healthcare provider data, medical insurance data, or other suitable data related to the healthcare provider search engine, subject to laws and regulations regarding patient data. Matching-engine system 160 may identify and rank healthcare providers in general, or according to one or more specified criteria, based on a verity of information. Matching-engine system 160 may be accessed by the other components of network environment 100 either directly or via network 110. In particular embodiments, matching-engine system 160 may receive inputs from one or more of a performance engine or an experience engine (which may be independent systems or sub-systems of matching-engine system 160). The performance engine may receive data about healthcare provider performance for a particular episode of care (e.g., from the healthcare providers directly, insurance companies, governmental agencies, patients, etc.) and calculate an estimated performance rating for an episode of care compared to a peer group of healthcare providers. The experience engine may receive data about healthcare provider experience (e.g., from public records, surveys, healthcare providers, rating sites, insurance companies, governmental agencies, patients, etc.) and calculate an estimated experience of the healthcare provider in general, or according to one or more specified criteria. In particular embodiments, matching-engine system 160 may include one or more servers 162. Each server 162 may be a unitary server or a distributed server spanning multiple computers or multiple datacenters. Servers 162 may be of various types, such as, for example and without limitation, web server, news server, mail server, message server, advertising server, file server, application server, exchange server, database server, proxy server, another server suitable for performing functions or processes described herein, or any combination thereof. In particular embodiments, each server 162 may include hardware, software, or embedded logic components or a combination of two or more such components for carrying out the appropriate functionalities implemented or supported by server 162. In particular embodiments, matching-engine system 164 may include one or more data stores 164. Data stores 164 may be used to store various types of information. In particular embodiments, the information stored in data stores 164 may be organized according to specific data structures. In particular embodiments, each data store 164 may be a relational, columnar, correlation, or other suitable database. Although this disclosure describes or illustrates particular types of databases, this disclosure contemplates any suitable types of databases. Particular embodiments may provide interfaces that enable a client system 130, a matching-engine system 160, or a third-party system 170 to manage, retrieve, modify, add, or delete, the information stored in data store 164.

In particular embodiments, matching-engine system 160 may be capable of linking a variety of entities. As an example and not by way of limitation, matching-engine system 160 may enable users to interact with each other as well as receive content from third-party systems 170 or other entities, or to allow users to interact with these entities through an application programming interfaces (API) or other communication channels.

In particular embodiments, a third-party system 170 may include one or more types of servers, one or more data stores, one or more interfaces, including but not limited to APIs, one or more web services, one or more content sources, one or more networks, or any other suitable components, e.g., that servers may communicate with. A third-party system 170 may be operated by a different entity from an entity operating matching-engine system 160. In particular embodiments, however, matching-engine system 160 and third-party systems 170 may operate in conjunction with each other to provide search engine services to users of matching-engine system 160 or third-party systems 170. In this sense, matching-engine system 160 may provide a platform, or backbone, which other systems, such as third-party systems 170, may use to provide search engine services and functionality to users across the Internet.

In particular embodiments, matching-engine system 160 also includes user-generated content objects, which may enhance a user's interactions with matching-engine system 160. User-generated content may include anything a user can add, upload, send, or "post" to matching-engine system 160. In particular embodiments, user-generated content may comprise user-profile information. As an example and not by way of limitation, a user communicates posts to matching-engine system 160 from a client system 130. Posts may include data such as health records, other textual data, location information, photos, videos, links, or other similar data or content. Content may also be added to matching-engine system 160 by a third-party (for example, from healthcare providers, insurance companies, etc.) through a suitable communication channel.

In particular embodiments, matching-engine system 160 may include a variety of servers, sub-systems, programs, modules, logs, and data stores. In particular embodiments, matching-engine system 160 may include one or more of the following: a web server, action logger, API-request server, relevance-and-ranking engine, content-object classifier, notification controller, action log, third-party-content-object-exposure log, inference module, authorization/privacy server, search module, advertisement-targeting module, user-interface module, user/patient-profile store, connection store, third-party content store, or location store. Matching-engine system 160 may also include suitable components such as network interfaces, security mechanisms, load balancers, failover servers, management-and-network-operations consoles, other suitable components, or any suitable combination thereof. In particular embodiments, matching-engine system 160 may include one or more user-profile stores for storing user profiles. A user/patient profile may include, for example, medical information, biographic information, demographic information, behavioral information, social information, or other types of descriptive information, such as work experience, educational history, hobbies or preferences, interests, affinities, or location. A web server may be used for linking matching-engine system 160 to one or more client systems 130 or one or more third-party system 170 via network 110. The web server may include a mail server or other messaging functionality for receiving and routing messages between matching-engine system 160 and one or more client systems 130. An API-request server may allow a third-party system 170 to access information from matching-engine system 160 by calling one or more APIs. An action logger may be used to receive communications from a web server about a user's actions on or off matching-engine system 160. In conjunction with the action log, a third-party-content-object log may be maintained of user exposures to third-party-content objects. A notification controller may provide information regarding content objects to a client system 130. Information may be pushed to a client system 130 as notifications, or information may be pulled from client system 130 responsive to a request received from client system 130. Authorization servers may be used to enforce one or more privacy settings of the users of matching-engine system 160. A privacy setting of a user determines how particular information associated with a user can be shared. The authorization server may allow users to opt in to or opt out of having their actions logged by matching-engine system 160 or shared with other systems (e.g., third-party system 170), such as, for example, by setting appropriate privacy settings. Third-party-content-object stores may be used to store content objects received from third parties, such as a third-party system 170. Location stores may be used for storing location information received from client systems 130 associated with users.

Systems and Methods

Figure 2:
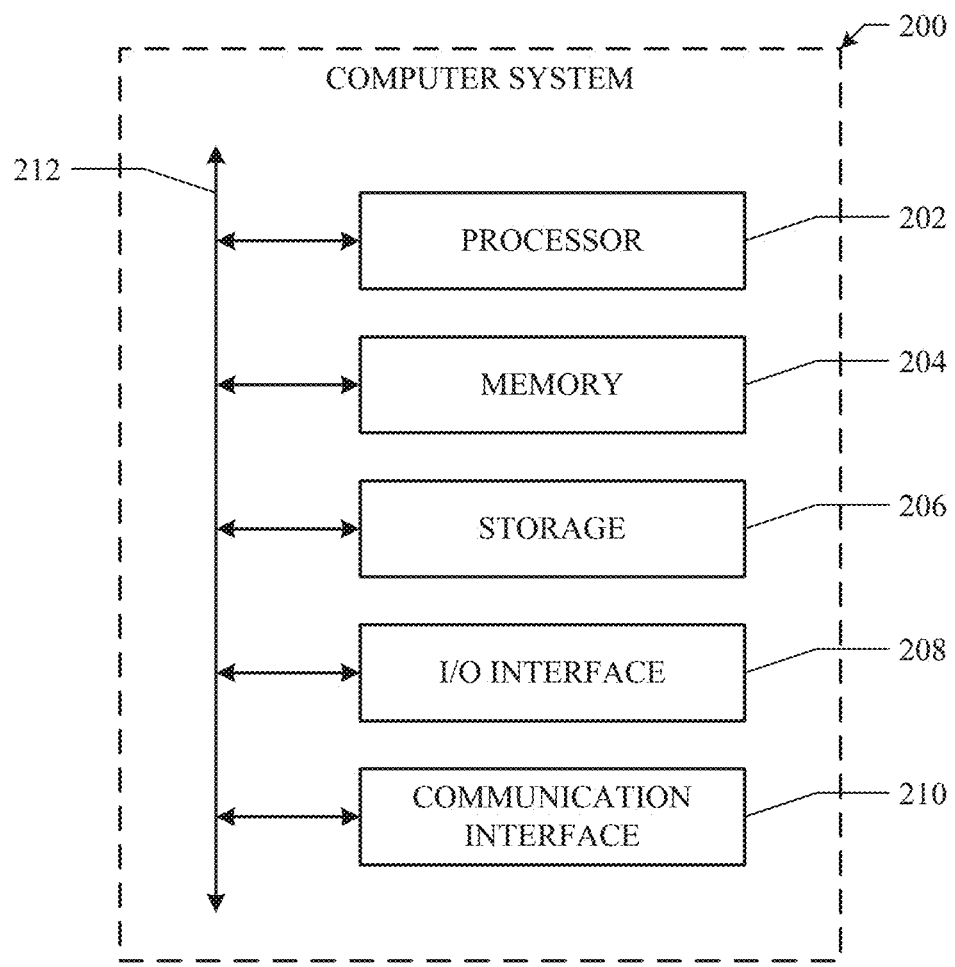
FIG. 2 illustrates an example computer system.

FIG. 2 illustrates an example computer system 200. In particular embodiments, one or more computer systems 200 perform one or more steps of one or more methods described or illustrated herein. In particular embodiments, one or more computer systems 200 provide functionality described or illustrated herein. In particular embodiments, software running on one or more computer systems 200 performs one or more steps of one or more methods described or illustrated herein or provides functionality described or illustrated herein. Particular embodiments include one or more portions of one or more computer systems 200. Herein, reference to a computer system may encompass a computing device, and vice versa, where appropriate. Moreover, reference to a computer system may encompass one or more computer systems, where appropriate.

This disclosure contemplates any suitable number of computer systems 200. This disclosure contemplates computer system 200 taking any suitable physical form. As example and not by way of limitation, computer system 200 may be an embedded computer system, a system-on-chip (SOC), a single-board computer system (SBC) (such as, for example, a computer-on-module (COM) or system-on-module (SOM)), a desktop computer system, a laptop or notebook computer system, an interactive kiosk, a mainframe, a mesh of computer systems, a mobile telephone, a personal digital assistant (PDA), a server, a tablet computer system, or a combination of two or more of these. Where appropriate, computer system 200 may include one or more computer systems 200; be unitary or distributed; span multiple locations; span multiple machines; span multiple data centers; or reside in a cloud, which may include one or more cloud components in one or more networks. Where appropriate, one or more computer systems 200 may perform without substantial spatial or temporal limitation one or more steps of one or more methods described or illustrated herein. As an example and not by way of limitation, one or more computer systems 200 may perform in real time or in batch mode one or more steps of one or more methods described or illustrated herein. One or more computer systems 200 may perform at different times or at different locations one or more steps of one or more methods described or illustrated herein, where appropriate.

In particular embodiments, computer system 200 includes a processor 202, memory 204, storage 206, an input/output (I/O) interface 208, a communication interface 210, and a bus 212. Although this disclosure describes and illustrates a particular computer system having a particular number of particular components in a particular arrangement, this disclosure contemplates any suitable computer system having any suitable number of any suitable components in any suitable arrangement.

In particular embodiments, processor 202 includes hardware for executing instructions, such as those making up a computer program. As an example and not by way of limitation, to execute instructions, processor 202 may retrieve (or fetch) the instructions from an internal register, an internal cache, memory 204, or storage 206; decode and execute them; and then write one or more results to an internal register, an internal cache, memory 204, or storage 206. In particular embodiments, processor 202 may include one or more internal caches for data, instructions, or addresses. This disclosure contemplates processor 202 including any suitable number of any suitable internal caches, where appropriate. As an example and not by way of limitation, processor 202 may include one or more instruction caches, one or more data caches, and one or more translation lookaside buffers (TLBs). Instructions in the instruction caches may be copies of instructions in memory 204 or storage 206, and the instruction caches may speed up retrieval of those instructions by processor 202. Data in the data caches may be copies of data in memory 204 or storage 206 for instructions executing at processor 202 to operate on; the results of previous instructions executed at processor 202 for access by subsequent instructions executing at processor 202 or for writing to memory 204 or storage 206; or other suitable data. The data caches may speed up read or write operations by processor 202. The TLBs may speed up virtual-address translation for processor 202. In particular embodiments, processor 202 may include one or more internal registers for data, instructions, or addresses. This disclosure contemplates processor 202 including any suitable number of any suitable internal registers, where appropriate. Where appropriate, processor 202 may include one or more arithmetic logic units (ALUs); be a multi-core processor; or include one or more processors 202. Although this disclosure describes and illustrates a particular processor, this disclosure contemplates any suitable processor.

In particular embodiments, memory 204 includes main memory for storing instructions for processor 202 to execute or data for processor 202 to operate on. As an example and not by way of limitation, computer system 200 may load instructions from storage 206 or another source (such as, for example, another computer system 200) to memory 204. Processor 202 may then load the instructions from memory 204 to an internal register or internal cache. To execute the instructions, processor 202 may retrieve the instructions from the internal register or internal cache and decode them. During or after execution of the instructions, processor 202 may write one or more results (which may be intermediate or final results) to the internal register or internal cache. Processor 202 may then write one or more of those results to memory 204. In particular embodiments, processor 202 executes only instructions in one or more internal registers or internal caches or in memory 204 (as opposed to storage 206 or elsewhere) and operates only on data in one or more internal registers or internal caches or in memory 204 (as opposed to storage 206 or elsewhere). One or more memory buses (which may each include an address bus and a data bus) may couple processor 202 to memory 204. Bus 212 may include one or more memory buses, as described below. In particular embodiments, one or more memory management units (MMUs) reside between processor 202 and memory 204 and facilitate accesses to memory 204 requested by processor 202. In particular embodiments, memory 204 includes random access memory (RAM). This RAM may be volatile memory, where appropriate. Where appropriate, this RAM may be dynamic RAM (DRAM) or static RAM (SRAM). Moreover, where appropriate, this RAM may be single-ported or multi-ported RAM. This disclosure contemplates any suitable RAM. Memory 204 may include one or more memories 204, where appropriate. Although this disclosure describes and illustrates particular memory, this disclosure contemplates any suitable memory.

In particular embodiments, storage 206 includes mass storage for data or instructions. As an example and not by way of limitation, storage 206 may include a hard disk drive (HDD), a floppy disk drive, flash memory, an optical disc, a magneto-optical disc, magnetic tape, or a Universal Serial Bus (USB) drive or a combination of two or more of these. Storage 206 may include removable or non-removable (or fixed) media, where appropriate. Storage 206 may be internal or external to computer system 200, where appropriate. In particular embodiments, storage 206 is non-volatile, solid-state memory. In particular embodiments, storage 206 includes read-only memory (ROM). Where appropriate, this ROM may be mask-programmed ROM, programmable ROM (PROM), erasable PROM (EPROM), electrically erasable PROM (EEPROM), electrically alterable ROM (EAROM), or flash memory or a combination of two or more of these. This disclosure contemplates mass storage 206 taking any suitable physical form. Storage 206 may include one or more storage control units facilitating communication between processor 202 and storage 206, where appropriate. Where appropriate, storage 206 may include one or more storages 206. Although this disclosure describes and illustrates particular storage, this disclosure contemplates any suitable storage.

In particular embodiments, I/O interface 208 includes hardware, software, or both, providing one or more interfaces for communication between computer system 200 and one or more I/O devices. Computer system 200 may include one or more of these I/O devices, where appropriate. One or more of these I/O devices may enable communication between a person and computer system 200. As an example and not by way of limitation, an I/O device may include a keyboard, keypad, microphone, monitor, mouse, printer, scanner, speaker, still camera, stylus, tablet, touch screen, trackball, video camera, another suitable I/O device or a combination of two or more of these. An I/O device may include one or more sensors. This disclosure contemplates any suitable I/O devices and any suitable I/O interfaces 208 for them. Where appropriate, I/O interface 208 may include one or more device or software drivers enabling processor 202 to drive one or more of these I/O devices. I/O interface 208 may include one or more I/O interfaces 208, where appropriate. Although this disclosure describes and illustrates a particular I/O interface, this disclosure contemplates any suitable I/O interface.

In particular embodiments, communication interface 210 includes hardware, software, or both providing one or more interfaces for communication (such as, for example, packet-based communication) between computer system 200 and one or more other computer systems 200 or one or more networks. As an example and not by way of limitation, communication interface 210 may include a network interface controller (NIC) or network adapter for communicating with an Ethernet or other wire-based network or a wireless NIC (WNIC) or wireless adapter for communicating with a wireless network, such as a WI-FI network. This disclosure contemplates any suitable network and any suitable communication interface 210 for it. As an example and not by way of limitation, computer system 200 may communicate with an ad hoc network, a personal area network (PAN), a local area network (LAN), a wide area network (WAN), a metropolitan area network (MAN), or one or more portions of the Internet or a combination of two or more of these. One or more portions of one or more of these networks may be wired or wireless. As an example, computer system 200 may communicate with a wireless PAN (WPAN) (such as, for example, a BLUETOOTH WPAN), a WI-FI network, a WI-MAX network, a cellular telephone network (such as, for example, a Global System for Mobile Communications (GSM) network), or other suitable wireless network or a combination of two or more of these. Computer system 200 may include any suitable communication interface 210 for any of these networks, where appropriate. Communication interface 210 may include one or more communication interfaces 210, where appropriate. Although this disclosure describes and illustrates a particular communication interface, this disclosure contemplates any suitable communication interface.

In particular embodiments, bus 212 includes hardware, software, or both coupling components of computer system 200 to each other. As an example and not by way of limitation, bus 212 may include an Accelerated Graphics Port (AGP) or other graphics bus, an Enhanced Industry Standard Architecture (EISA) bus, a front-side bus (FSB), a HYPERTRANSPORT (HT) interconnect, an Industry Standard Architecture (ISA) bus, an INFINIBAND interconnect, a low-pin-count (LPC) bus, a memory bus, a Micro Channel Architecture (MCA) bus, a Peripheral Component Interconnect (PCI) bus, a PCI-Express (PCIe) bus, a serial advanced technology attachment (SATA) bus, a Video Electronics Standards Association local (VLB) bus, or another suitable bus or a combination of two or more of these. Bus 212 may include one or more buses 212, where appropriate. Although this disclosure describes and illustrates a particular bus, this disclosure contemplates any suitable bus or interconnect.

Herein, a computer-readable non-transitory storage medium or media may include one or more semiconductor-based or other integrated circuits (ICs) (such, as for example, field-programmable gate arrays (FPGAs) or application-specific ICs (ASICs)), hard disk drives (HDDs), hybrid hard drives (HHDs), optical discs, optical disc drives (ODDs), magneto-optical discs, magneto-optical drives, floppy diskettes, floppy disk drives (FDDs), magnetic tapes, solid-state drives (SSDs), RAM-drives, SECURE DIGITAL cards or drives, any other suitable computer-readable non-transitory storage media, or any suitable combination of two or more of these, where appropriate. A computer-readable non-transitory storage medium may be volatile, non-volatile, or a combination of volatile and non-volatile, where appropriate.

This disclosure contemplates one or more computer-readable storage media implementing any suitable storage. In particular embodiments, a computer-readable storage medium implements one or more portions of processor 202 (such as, for example, one or more internal registers or caches), one or more portions of memory 204, one or more portions of storage 206, or a combination of these, where appropriate. In particular embodiments, a computer-readable storage medium implements RAM or ROM. In particular embodiments, a computer-readable storage medium implements volatile or persistent memory. In particular embodiments, one or more computer-readable storage media embody software. Herein, reference to software may encompass one or more applications, bytecode, one or more computer programs, one or more executables, one or more instructions, logic, machine code, one or more scripts, or source code, and vice versa, where appropriate. In particular embodiments, software includes one or more application programming interfaces (APIs). This disclosure contemplates any suitable software written or otherwise expressed in any suitable programming language or combination of programming languages. In particular embodiments, software is expressed as source code or object code. In particular embodiments, software is expressed in a higher-level programming language, such as, for example, C, Perl, or a suitable extension thereof. In particular embodiments, software is expressed in a lower-level programming language, such as assembly language (or machine code). In particular embodiments, software is expressed in JAVA. In particular embodiments, software is expressed in Hyper Text Markup Language (HTML), Extensible Markup Language (XML), JavaScript Object Notation (JSON) or other suitable markup language.

Figure 3:
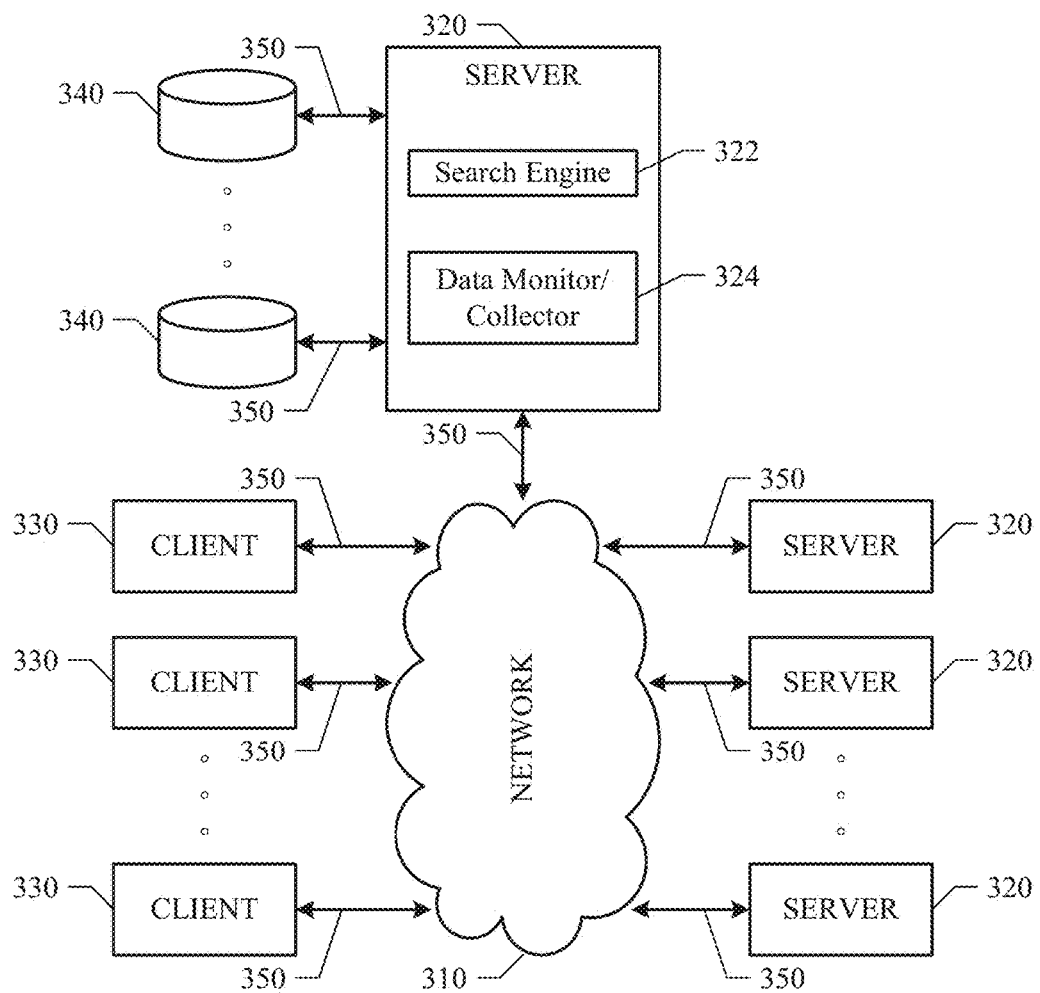
FIG. 3 illustrates an example network environment.

FIG. 3 illustrates an example network environment 300. This disclosure contemplates any suitable network environment 300. As an example and not by way of limitation, although this disclosure describes and illustrates a network environment 300 that implements a client-server model, this disclosure contemplates one or more portions of a network environment 300 being peer-to-peer, where appropriate. Particular embodiments may operate in whole or in part in one or more network environments 300. In particular embodiments, one or more elements of network environment 300 provide functionality described or illustrated herein. Particular embodiments include one or more portions of network environment 300. Network environment 300 includes a network 310 coupling one or more servers 320 and one or more clients 330 to each other. This disclosure contemplates any suitable network 310. As an example and not by way of limitation, one or more portions of network 310 may include an ad hoc network, an intranet, an extranet, a virtual private network (VPN), a local area network (LAN), a wireless LAN (WLAN), a wide area network (WAN), a wireless WAN (WWAN), a metropolitan area network (MAN), a portion of the Internet, a portion of the Public Switched Telephone Network (PSTN), a cellular telephone network, or a combination of two or more of these. Network 310 may include one or more networks 310.

Links 350 couple servers 320 and clients 330 to network 310 or to each other. This disclosure contemplates any suitable links 350. As an example and not by way of limitation, one or more links 350 each include one or more wireline (such as, for example, Digital Subscriber Line (DSL) or Data Over Cable Service Interface Specification (DOCSIS)), wireless (such as, for example, Wi-Fi or Worldwide Interoperability for Microwave Access (WiMAX)) or optical (such as, for example, Synchronous Optical Network (SONET) or Synchronous Digital Hierarchy (SDH)) links 350. In particular embodiments, one or more links 350 each includes an intranet, an extranet, a VPN, a LAN, a WLAN, a WAN, a MAN, a communications network, a satellite network, a portion of the Internet, or another link 350 or a combination of two or more such links 350. Links 350 need not necessarily be the same throughout network environment 300. One or more first links 350 may differ in one or more respects from one or more second links 350.

This disclosure contemplates any suitable servers 320. As an example and not by way of limitation, one or more servers 320 may each include one or more advertising servers, applications servers, catalog servers, communications servers, database servers, exchange servers, fax servers, file servers, game servers, home servers, mail servers, message servers, news servers, name or DNS servers, print servers, proxy servers, sound servers, standalone servers, web servers, or web-feed servers. In particular embodiments, a server 320 includes hardware, software, or both for providing the functionality of server 320. As an example and not by way of limitation, a server 320 that operates as a web server may be capable of hosting websites containing web pages or elements of web pages and include appropriate hardware, software, or both for doing so. In particular embodiments, a web server may host HTML or other suitable files or dynamically create or constitute files for web pages on request. In response to a Hyper Text Transfer Protocol (HTTP) or other request from a client 330, the web server may communicate one or more such files to client 330. As another example, a server 320 that operates as a mail server may be capable of providing e-mail services to one or more clients 330. As another example, a server 320 that operates as a database server may be capable of providing an interface for interacting with one or more data stores (such as, for example, data stores 340 described below). Where appropriate, a server 320 may include one or more servers 320; be unitary or distributed; span multiple locations; span multiple machines; span multiple datacenters; or reside in a cloud, which may include one or more cloud components in one or more networks.

In particular embodiments, one or more links 350 may couple a server 320 to one or more data stores 340. A data store 340 may store any suitable information, and the contents of a data store 340 may be organized in any suitable manner. As an example and not by way or limitation, the contents of a data store 340 may be stored as a dimensional, flat, hierarchical, network, object-oriented, relational, XML, NoSQL, Hadoop, or other suitable database or a combination or two or more of these. A data store 340 (or a server 320 coupled to it) may include a database-management system or other hardware or software for managing the contents of data store 340. The database-management system may perform read and write operations, delete or erase data, perform data deduplication, query or search the contents of data store 340, or provide other access to data store 340.

In particular embodiments, one or more servers 320 may each include one or more search engines 322. A search engine 322 may include hardware, software, or both for providing the functionality of search engine 322. As an example and not by way of limitation, a search engine 322 may implement one or more search algorithms to identify network resources in response to search queries received at search engine 322, one or more ranking algorithms to rank identified network resources, or one or more summarization algorithms to summarize identified network resources. In particular embodiments, a ranking algorithm implemented by a search engine 322 may use a machine-learned ranking formula, which the ranking algorithm may obtain automatically from a set of training data constructed from pairs of search queries and selected Uniform Resource Locators (URLs), where appropriate.

In particular embodiments, one or more servers 320 may each include one or more data monitors/collectors 324. A data monitor/collection 324 may include hardware, software, or both for providing the functionality of data collector/collector 324. As an example and not by way of limitation, a data monitor/collector 324 at a server 320 may monitor and collect network-traffic data at server 320 and store the network-traffic data in one or more data stores 340. In particular embodiments, server 320 or another device may extract pairs of search queries and selected URLs from the network-traffic data, where appropriate.

This disclosure contemplates any suitable clients 330. A client 330 may enable a user at client 330 to access or otherwise communicate with network 310, servers 320, or other clients 330. As an example and not by way of limitation, a client 330 may have a web browser, such as MICROSOFT INTERNET EXPLORER or MOZILLA FIREFOX, and may have one or more add-ons, plug-ins, or other extensions, such as GOOGLE TOOLBAR or YAHOO TOOLBAR. A client 330 may be an electronic device including hardware, software, or both for providing the functionality of client 330. As an example and not by way of limitation, a client 330 may, where appropriate, be an embedded computer system, an SOC, an SBC (such as, for example, a COM or SOM), a desktop computer system, a laptop or notebook computer system, an interactive kiosk, a mainframe, a mesh of computer systems, a mobile telephone, a PDA, a netbook computer system, a server, a tablet computer system, or a combination of two or more of these. Where appropriate, a client 330 may include one or more clients 330; be unitary or distributed; span multiple locations; span multiple machines; span multiple datacenters; or reside in a cloud, which may include one or more cloud components in one or more networks.

Matching Engine

Using search engine systems to search for physicians may be problematic because many available regarding physicians, particularly regarding their prior experience with respect to particular medical conditions, symptoms, or procedures, may not be readily available. Consequently, for a user to search for an appropriate physician may require multiple queries, and researching multiple sources for information regarding physicians, utilizing large amounts of time and network resources. A matching engine such as matching-engine system 160 may be relevant for reducing the overall number of searches conducted by a user seeking to find a physician for a particular symptom or diagnosis by tailoring a search query to reference one or more base concepts, which are based on a particular medical diagnosis or treatment, then identifying physicians who have a satisfactory experience score and performance score specifically for that base concept. This may reduce the total number of queries conducted by the user and the total number of references accessed by the user, thereby reducing the overall bandwidth and data sent by a computing device of the user to be handled by matching-engine system 160. In particular embodiments, by determining an initial set of physicians suitable to the user's search, matching-engine system 160 may provide more relevant information for the user even based on a broad search, thereby precluding the necessity for the user to perform multiple searches in order to narrow down to a specific physician.

In particular embodiments, a user of matching-engine system 160 may send a query to matching-engine system 160 for a recommendation of one or more physicians. The query may comprise a specific medical condition, one or more symptoms, one or more names of a medical specialty, or a type of medical procedure. As an example and not by way of limitation, a user may send a query regarding physicians to treat plantar fasciitis. As another example, a user may send a query merely stating that the user has a headache and nausea, and request one or more physicians to help with the user's symptoms. As another example, a user may send a query for physicians able to perform a colonoscopy. In particular embodiments, a user may send separate queries for one or more symptoms, conditions, or treatments. In particular embodiments, a user may send a single query containing several distinct symptoms, conditions, or treatments. As an example and not by way of limitation, a user may submit a query that comprises an indication that the user needs an annual physical, and also that the user has stomach pains. Matching-engine system 160 may provide the user with a set of recommended physicians for an annual physical, and a second set of recommended physicians for the stomach pain. In particular embodiments, matching-engine system 160 may send the user a single set of recommended physicians, wherein the set comprises recommended physicians for the annual physical and recommended physicians for the stomach pain. In particular embodiments, there may be an overlap between the two different sets of recommended physicians.

In particular embodiments, matching-engine system 160 may recommend one or more physicians for a user to visit within a particular geographic region in which the user resides or works. In particular embodiments, the geographic region may be a metropolitan statistical area (MSA). MSAs are defined metropolitan regions determined by the United States Office of Management and Budget. As an example and not by way of limitation, matching-engine system 160 may recommend physicians who are located within the Los Angeles-Long Beach-Anaheim MSA. In particular embodiments, matching-engine system 160 may recommend one or more physicians who are within a preset distance of the location of the user. As an example and not by way of limitation, matching-engine system 160 may only recommend physicians who are within 25 miles of the user. In particular embodiments, the user may specify a distance or region in which to look for physicians to recommend. As an example and not by way of limitation, a user may indicate that she only wants to view recommended physicians within Orange County, Calif., without receiving recommendations for physicians within Los Angeles, Calif.

In particular embodiments, parameters for recommending one or more physicians to a user may be provided by an administrator of the particular user's health plan. As an example and not by way of limitation, if a user receives her health insurance coverage through her employment, and her employer has an administrator responsible for determining the health-care coverage to be provided by the employer, then the administrator may specify an acceptable range of parameters within which to recommend physicians. For example, the administrator may wish to specify a range of acceptable performance scores for physicians, acceptable monetary costs for physicians when conducting particular treatments or procedures, or an acceptable range of experience indices for physicians. In particular embodiments, performance score may represent a physician's efficiency in time and resources in treating a patient for a particular condition or disease, or in applying a particular treatment method. A performance score may be of interest to both a patient and the patient's insurance provider as an indication that a physician will require less time, office visits, resources, etc. In particular embodiments, an experience index for a physician may indicate the physician's experience in dealing with a particular condition or disease, or in performing a particular treatment method. In particular embodiments, the experience index may also represent how many different types of conditions within a condition group a physician has seen. These parameters may allow the administrator to direct users towards physicians that the administrator has determined are cost-effective physicians, or in the alternative, physicians that are above a threshold baseline of competency while remaining affordable for the employer. In particular embodiments, when a user of the health-care plan run by that administrator submits a query for one or more physicians, matching-engine system 160 may only present physicians meeting the acceptable parameters specified by the administrator. In particular embodiments, matching-engine system 160 may include other physicians, but may rank the physicians meeting the administrator's parameters more highly.

Figure 4:
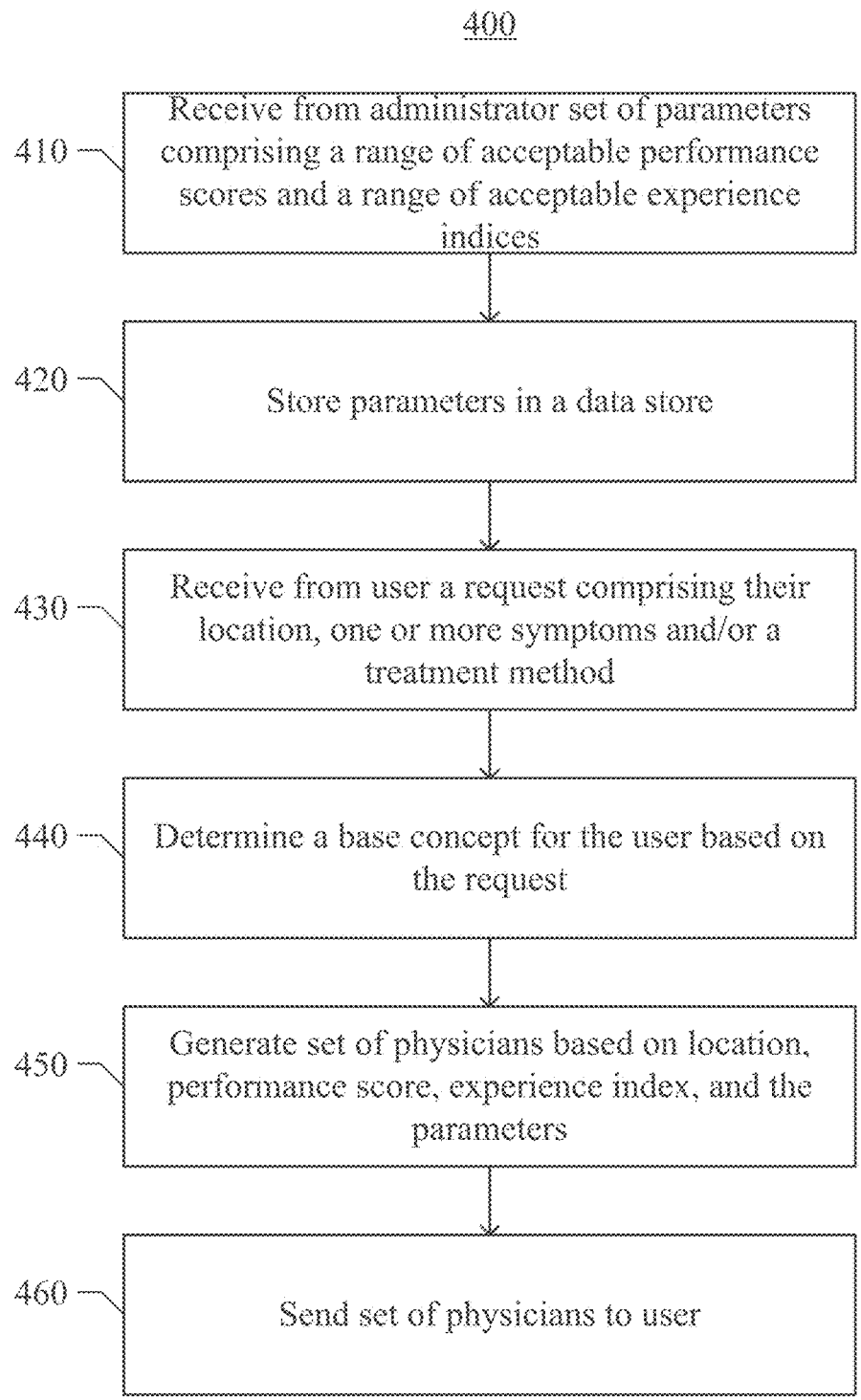
FIG. 4 illustrates an example method of using a matching-engine system.

FIG. 4 illustrates an example method for using matching-engine system 160 to provide one or more recommended physicians to a particular user. At step 410, matching-engine system 160 may receive from an administrator a set of parameters. In particular embodiments, the set of parameters may comprise a range of acceptable performance scores, a range of acceptable experience indices, or a range of acceptable costs. At step 420, matching-engine system 160 may store the set of parameters in a database, associating the set of parameters with a group of one or more users corresponding to the administrator. As an example and not by way of limitation, the group of users may comprise the employees on an employer-provided health-care plan. At step 430, matching-engine system 160 may receive from one of the group of users a request, wherein the request comprises at least the user's geographic location, and one or more symptoms or a treatment method. As an example and not by way of limitation, user Alice may send a request which includes information indicating that she resides in Mountain View, Calif., and she has stomach pains and nausea. As another example, user Zeke may send a request which includes information indicating that his location is Evanston, Ill., and he is seeking a physician for rotator cuff surgery. At step 440, matching-engine system 160 may determine at least one base concept associated with the user's request. As an example and not by way of limitation, in the examples given above, matching-engine system 160 may determine a base concept of "rotator cuff surgery" for Zeke, and a base concept of "stomach ache" for Alice. At step 450, matching-engine system 160 may generate a set of one or more physicians to recommend to the user for the determined base concept. Matching-engine system 160 may also consider the location of the user and locations of the physicians, and the performance scores and experience indices for each physician relevant to the base concept, and whether they are within the parameters defined by the administrator. At step 460, matching-engine system 160 may send the set of recommended physicians to the user.

Particular embodiments may repeat one or more steps of the method of FIG. 4, where appropriate. Although this disclosure describes and illustrates particular steps of the method of FIG. 4 as occurring in a particular order, this disclosure contemplates any suitable steps of the method of FIG. 4 occurring in any suitable order. Moreover, although this disclosure describes and illustrates particular components, devices, or systems carrying out particular steps of the method of FIG. 4, this disclosure contemplates any suitable combination of any suitable components, devices, or systems carrying out any suitable steps of the method of FIG. 4.

In particular embodiments, matching-engine system 160 may receive as an input one or more performance scores associated with particular physicians in generating a set of recommended physicians. Matching-engine system 160 may receive from a physician or health-care provider one or more Current Procedural Terminology (CPT) codes, each of which corresponds to a medical, surgical, or diagnostic service. As an example and not by way of limitation, matching-engine system 160 may receive a CPT code for patient Alice after a visit to Dr. Bob, which may indicate that patient Alice received a standard blood panel test. Matching-engine system 160 may also receive one or more International Classification of Diseases (ICD) codes, each of which corresponds to a particular disease or condition. In particular embodiments, an insurance provider may not pay for medical services provided to a particular insured patient unless the CPT codes for the services provided correlate with the ICD codes assigned to that particular patient visit. As an example and not by way of limitation, an insurance provider may reject for payment the charges for a CPT code indicating a colonoscopy, if the only ICD code assigned to the patient visit indicates that the visit was for a sore throat.

In particular embodiments, the costs incurred by a physician in treating a patient may be considered in monetary cost. In particular embodiments, another metric may be used to calculate costs incurred for treatment which accounts for monetary costs as well as labor costs and overall resources involved for the treatment. As an example and not by way of limitation, matching-engine system 160 may consider the costs in terms of resource value units, or RVUs. As an example and not by way of limitation, matching-engine system 160 may use RVUs as used by the United States Medicare reimbursement formula for physician services. An RVU may represent a non-monetary relative measure which is scaled by the geographic region in which the treatment occurred. As an example and not by way of limitation, in monetary costs, the same medical procedure may be more expensive in a high cost-of-living area compared to a low cost-of-living area. By adjusting for the cost-of-living or the average cost of medical services in a given area, the RVU may comprise a location-independent measure of costs. In particular embodiments, an RVU may be assigned to each CPT code for particular treatments. In particular embodiments, RVUs may be assigned in advance, such that matching-engine system 160 may receive a CPT code and automatically add the appropriate RVU to the episode of care.

In particular embodiments, matching-engine system 160 may receive the monetary costs for a particular service or treatment as an additional cost factor to the RVU. In particular embodiments, the cost may be a reported average monetary cost per patient per year for a particular base concept, which may be calculated based on the received cost figures during the previous year. In particular embodiments, the average costs per patient per year may be an expected cost for treating the patient. This expected cost may then be compared against the actual costs incurred by a physician in treating the patient, by converting the RVUs incurred in treatment back into monetary costs. As an example and not by way of limitation, the average cost per year for treating a particular disease may be expected to be $7,500. If a physician treating the disease may incur costs of 120 RVUs, and the conversion rate for an RVU in this particular specialty is estimated at $55.00/RVU, then the actual costs incurred by this physician in treating the disease may be 120'$55.00, or $6,600. Comparing the RVU costs to the estimated costs may show that this physician is $900 more efficient in treating this particular disease than expected. In particular embodiments, matching-engine system 160 may include other factors in calculating a performance score, such as administrative costs or non-physician services costs. As an example and not by way of limitation, if a first treatment method requires five office visits, and a second treatment method requires two office visits, matching-engine system 160 may determine that the first treatment method will have higher additional costs in terms of time required by the patient, and administrative costs in processing additional office visits.

In particular embodiments, a performance score for a physician may reflect an indication of the amount of health-care resources used by the physician or health-care provider in delivery of care for treating patients with the same or similar clinical complexity. Complex treatments may result in more resources being consumed than simple cases regardless of physician skills, but there may be a variation in how much resources are used. The performance score may identify physicians who are using relatively less resources than the peer group, and by how much. Determination of the performance score is discussed in further detail below.

In particular embodiments, matching-engine system 160 may also receive and use as an input one or more experience indices associated with a particular physician. The experience index for a physician may be an indication of how much experience a physician has in a particular specialty or with a particular disease or condition, based on the number of patients seen with the particular specialty or disease or condition, and the severity of each patient seen. In particular embodiments, matching-engine system 160 may consider the case volume seen by a particular physician within a particular specialty, which may represent a proportional volume of cases for a particular disease seen by the particular physician versus all other physicians in the same specialty. As an example and not by way of limitation, if there were 100 separate patient visits for diagnosis or treatment of non-Hodgkins lymphoma in the Chicago metropolitan area in the year 2013, and 25 of those visits were to Dr. Moore, matching-engine system 160 may consider Dr. Moore's case volume for non-Hodgkins lymphoma to be 0.25, or 25 divided by the 100 total cases. In particular embodiments, the experience index may also represent a variety of diseases seen by a particular physician within a particular specialty. In particular embodiments, the experience index may consider three factors: volume, variety, and severity. The severity may be measured by a Boolean scale: chronic, or non-chronic, using the Chronic Conditions Indication database from the Healthcare Cost Institute. Determination of the experience index is discussed in detail further below.

In particular embodiments, physicians in the determined set of physicians may be scored on a number of statistics in comparison to their peer group. In particular embodiments, the statistics may be received by matching-engine system 160 based upon the medical records associated with each physician. In particular embodiments, the statistics may be determined from information received from insurance information associated with patients with respect to each physician. As an example and not by way of limitation, matching-engine system 160 may determine a particular physician's 30-day readmission rate, which is the rate at which patients treated by the particular physician are readmitted to a healthcare facility within 30 days of receiving treatment from the particular physician, as compared to the peer group. In particular embodiments, the readmission rate may be for any predetermined time period. In particular embodiments, a higher readmission rate may result in a lower performance-score or a lower overall score for the physician.

In particular embodiments, matching-engine system 160 may determine a rate of post-surgical infections or other post-treatment complications for the particular physician compared to the peer group. As an example and not by way of limitation, matching-engine system 160 may determine, for a particular period of time following treatment by the physician, whether a patient is diagnosed with an infection or other complication related to the treatment. In particular embodiments, a higher reinfection rate may result in a lower performance-score or a lower overall score for the physician.

In particular embodiments, matching-engine system 160 may calculate an average length-of-stay for patients who are seen by the particular physician for a particular condition or treatment, compared to the average length-of-stay for the peer group. As an example and not by way of limitation, matching-engine system 160 may determine how long a physician's patients stay in a healthcare facility such as a hospital for a particular base-concept. In particular embodiments, a longer average length-of-stay may result in a lower performance-score or a lower overall score for the physician.

In particular embodiments, matching-engine system 160 may consider the relative invasiveness of procedures used by the particular physician, compared to the invasiveness of procedures used by the peer group of physicians. In particular embodiments, each procedure may be associated with a particular value indicating its invasiveness. In particular embodiments, a patient may desire less invasive procedures if they are equally effective or even nearly as effective. In particular embodiments, a physician with a relatively higher invasiveness value may be assigned a lower performance-score or a lower overall score.

In particular embodiments, matching-engine system 160 may also consider the ratings for the healthcare facility in which the particular physician practices. In particular embodiments, a healthcare facility rating may be assigned by matching-engine system 160, or by any other suitable entity for rating facilities. As an example and not by way of limitation, matching-engine system 160 may assign a higher performance-score or a higher overall score to a physician practicing at a higher-rated facility since that may affect issues such as infection, readmission, length-of-stay, etc.

In particular embodiments, matching-engine system 160 may calculate a patient-risk-score for each user making a search query on matching-engine system 160. The patient-risk-score may be a quantitative prediction of a number of medical resources that the particular user is likely to require for a future time period. The prediction of resource-use may be based on information known about the user, such as demographic information, information associated with behavior or lifestyle of the user, or medical records of the user. The medical records may indicate a number of concurrent diseases that the user has (e.g. comorbidities), an indication of how many of the comorbidities are chronic conditions, previous medical diagnoses received and treatment received. In particular embodiments, the records of medical treatments or procedures that the user has received may indicate a value of resource usage for those treatments and procedures. Based on the past resource usage, medical history, and information about the user, matching-engine system 160 may be able to predict the resource-use for the user, compare the user's resource-use to that of a patient population which includes the user, and assign the user a patient-risk-score indicating a relative predicted resource-use compared to the patient population. In particular embodiments, a user making a search query on matching-engine system 160 may know precisely what medical condition he wishes to have treated, or a specific medical treatment that the user may want performed on him. As an example and not by way of limitation, a user may make a search query specifically for "total knee replacement", knowing that he needs this procedure, and matching-engine system 160 may then provide the user with a list of orthopedic surgeons specializing in knee replacement surgeries and in particular total knee replacement surgeries. In particular embodiments, a user may have a general sense of what they are searching for. As an example and not by way of limitation, a user may have knee pain, without knowing what is causing it or what treatment options are available. If this user searches for "total knee replacement", the set of search results (i.e. the list of orthopedic surgeons specializing in knee replacements) may not be as useful to the user; the user may visit the orthopedic surgeon only to have to go back to a general practitioner, a radiologist, or other healthcare provider before the knee replacement can be scheduled. As another example, it may turn out that the user doesn't need a total knee replacement at all. In these examples, having a user select "total knee replacement" is not an efficient treatment path, as additional or unnecessary office visits and test may occur. Further discussion of patient risk and providing search results to a user based on the user's risk score is provided in U.S. patent application Ser. No. 15/079,567, filed Mar. 24, 2016, which is incorporated herein by reference.

Performance Engine

In particular embodiments, a performance engine of matching-engine system 160 may determine one or more performance scores for a particular physician based on data received about episodes of care associated with the particular physician. An episode of care may represent all interactions between a patient and a physician for a particular disease or treatment. In particular embodiments, using an episode of care as the base point for determining performance scores may be more accurate than determining performance merely based on cost. As an example and not by way of limitation, if Dr. Alan has a lower average cost than Dr. Brad for medical services, but Dr. Alan requires more tests and more office visits to treat the same disease as Dr. Brad, the individual service costs may point to Dr. Alan as having better performance (e.g. lower cost for the same services), but the overall episode of care may point to Dr. Brad as having better overall performance in treating the disease, which may be a better indicator of doctor efficiency.

In particular embodiments, an episode of care may comprise a collection of all clinically related procedure and diagnosis codes for treating an index disease or condition for a particular patient from the onset of the index disease or condition to closure. An episode of care may comprise a record of all encounters between a patient and a health-care provider. In particular embodiments, an episode of care may be defined over a single calendar year. As an example and not by way of limitation, if a patient Alice starts visiting a doctor Bob for her Type-2 diabetes on Jul. 1, 2013, and continues to see Dr. Bob for her diabetes with monthly visits through August, 2014, matching-engine system 160 may consider Alice to have two episodes of care with Dr. Bob: one episode of care for diabetes in 2013, and a second episode of care for diabetes in 2014. In particular embodiments, a particular patient may only be associated with a single episode of care at a time. If the patient starts visiting a new doctor, or starts being treated for a new primary condition, a new episode of care may be determined. As an example and not by way of limitation, if Alice has been visiting Dr. Bob for her diabetes through August 2014, but then breaks her leg and starts seeing Dr. Bob for treatment of the broken leg for two months, matching-engine system 160 may determine a new episode of care for Alice and Dr. Bob with a new primary condition of "broken leg" from August 2014 to October 2014. If Alice's leg heals and she continues seeing Dr. Bob for her diabetes, matching-engine system 160 may determine a third episode of care for Alice and Dr. Bob for diabetes. In particular embodiments, matching-engine system 160 may determine a single episode of care for 2014 for Alice and Dr. Bob for a primary condition of diabetes, with a time period of January to August 2014, and October to December 2014.

In particular embodiments, an episode of care may be associated with a single base concept. The base concept may represent the primary disease or condition being treated by the visits comprising the episode of care. In particular embodiments, the base concept may be identified using a clinical taxonomy. A clinical taxonomy may comprise a table of medical terminology with corresponding laymen's terms for the medical term. As an example and not by way of limitation, a patient may visit a doctor for a "broken leg." Matching-engine system 160 may determine record the visit as an episode of care with a base concept of "tibial plateau fracture." In particular embodiments, matching-engine system 160 may additionally record one or more sub-concepts associated with the base concept. Each sub-type may represent an additional diagnoses, conditions or diseases that the patient has which could introduce complications in treatment of the base concept. As an example and not by way of limitation, if a patient who is making a physician visit for a broken leg also has osteoporosis, matching-engine system 160 may record an episode of care as having a base concept of "tibial plateau fracture," with a sub-concept of "osteoporosis." Including the sub-types may ensure that physicians are not evaluated simply based on how they are able to treat the base concept. The simultaneous presence of additional conditions in a patient may likely create additional resource burdens, which may lead to additional treatment costs. As an example and not by way of limitation, if Dr. Bob is treating a patient for a broken leg with no other sub-concepts involved, and Dr. Charles is treating a patient for a broken leg with a sub-concept of osteoporosis, Dr. Charles may require additional resources in treating the base concept condition of the broken leg. However, comparing the two episodes of care without any adjustment for the sub-concept may not accurately represent each physician's performance in treating a broken leg, and may lead to false negatives in evaluation of the physicians.

In particular embodiments, the performance score for a particular physician may be represented as a relational score for the particular physician with respect to similarly-situated physicians. In particular embodiments, similarly-situated physicians may additionally be defined as seeing a similar set of patients which are characterized by attributes of age, gender, place of service, MSA, and disease co-morbidity. In particular embodiments, additional attributes may be used to determine similarly-situated physicians. In particular embodiments, matching-engine system 160 may consider physicians having the same primary specialty. As an example and not by way of limitation, matching-engine system 160 may generate a score that indicates the particular physician's efficiency and performance compared to other physicians that the user may also receive recommendations for. For example, if Drs. Irene, John, and Kyle are the three nephrologists in a particular geographic region, any performance score for Dr. John may represent his relative performance when compared to Drs. Irene and Kyle.

Figure 5:
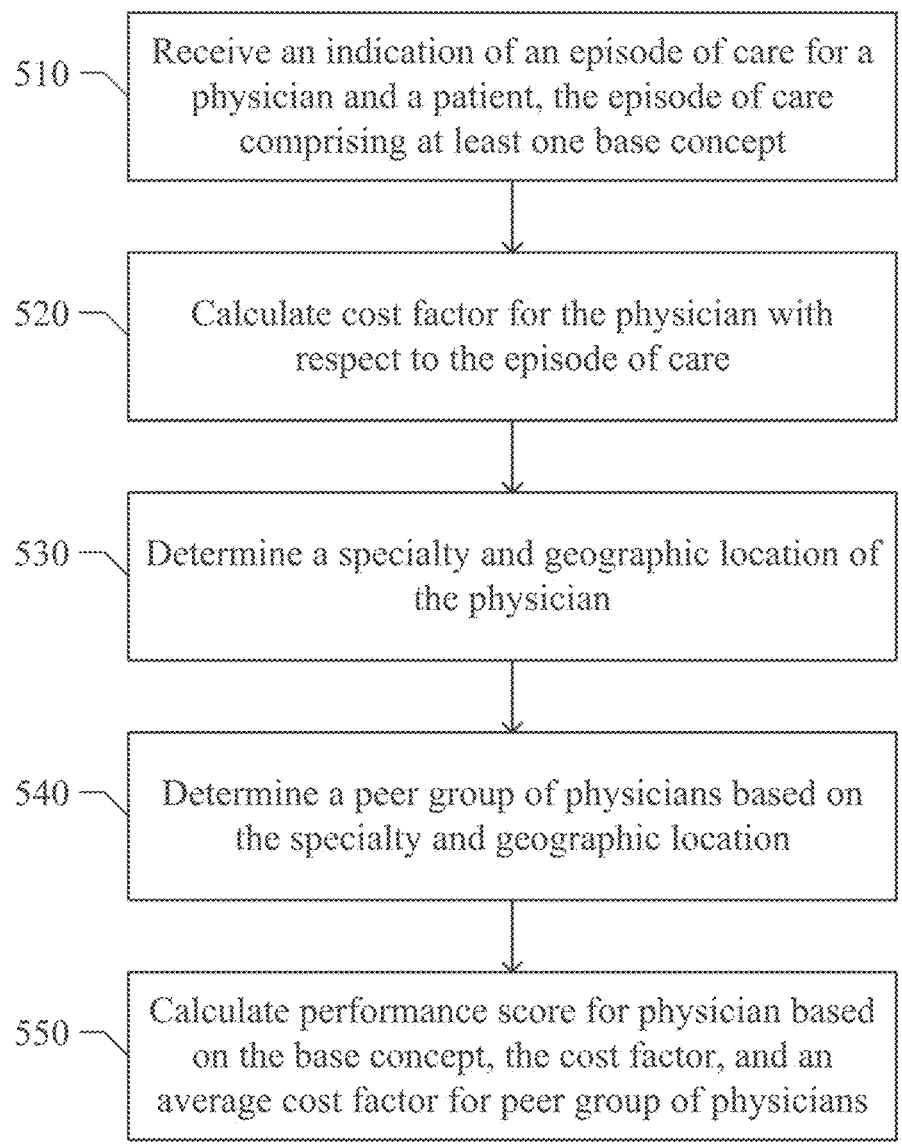
FIG. 5 illustrates an example method of calculating a performance score using a performance engine.

FIG. 5 illustrates an example method for determining a performance score for a physician with respect to a particular episode of care. The method may begin at step 510, where matching-engine system 160 may receive an indication of an episode of care for a particular physician and a particular patient. The indication may comprise a number of diagnosis and treatment codes, such as a set of related CPT codes and ICD codes. Based on the received codes, matching-engine system 160 may determine a base concept for the episode of care. In particular embodiments, matching-engine system 160 may determine one or more sub-concepts that are associated with the base concept of the episode of care. As an example and not by way of limitation, matching-engine system 160 may receive CPT and/or ICD codes within the episode of care that indicate that the patient has at least one secondary condition. At step 520, matching-engine system 160 may calculate a cost factor for the episode of care for the particular physician. In particular embodiments, the cost factor may be the monetary cost of the treatments within the episode of care. In particular embodiments, the cost factor may be a normalized value, such as RVU. In particular embodiments, matching-engine system 160 may consider both the absolute monetary costs expended in treating the episode of care, as well as the RVU. At step 530, matching-engine system 160 may determine at least one specialty of the physician, and a geographic area that the physician practices in. At step 540, the specialty and geographic area of the physician may be used to determine a peer group of one or more other physicians who share a common specialty and practice within the same geographic area as the particular physician. As an example and not by way of limitation, if Dr. Chad is a cardiologist practicing in Denver, Colo., his peer group may be all cardiologists practicing in the Denver area. At step 550, matching-engine system 160 may calculate a performance score for the particular physician with respect to the base concept and the sub-concepts by comparing the cost factor for the episode of care with the cost factors incurred by the peer group of physicians for the same base concept and sub-concepts. As an example and not by way of limitation, if Dr. Chad has an episode of care for a patient with a myocardial infarction and a sub-concept of diabetes, matching-engine system 160 may compare the costs incurred by Dr. Chad for this episode of care with the costs associated with other episodes of care by the other physicians in the peer group with a base concept of myocardial infarction and a sub-concept of diabetes. In particular embodiments, matching-engine system 160 may further determine whether the other physicians in the peer group are seeing patients with similar attributes such as age, gender, place of service, and MSA.

Particular embodiments may repeat one or more steps of the method of FIG. 5, where appropriate. Although this disclosure describes and illustrates particular steps of the method of FIG. 5 as occurring in a particular order, this disclosure contemplates any suitable steps of the method of FIG. 5 occurring in any suitable order. Moreover, although this disclosure describes and illustrates particular components, devices, or systems carrying out particular steps of the method of FIG. 5, this disclosure contemplates any suitable combination of any suitable components, devices, or systems carrying out any suitable steps of the method of FIG. 5.

Figure 6A:
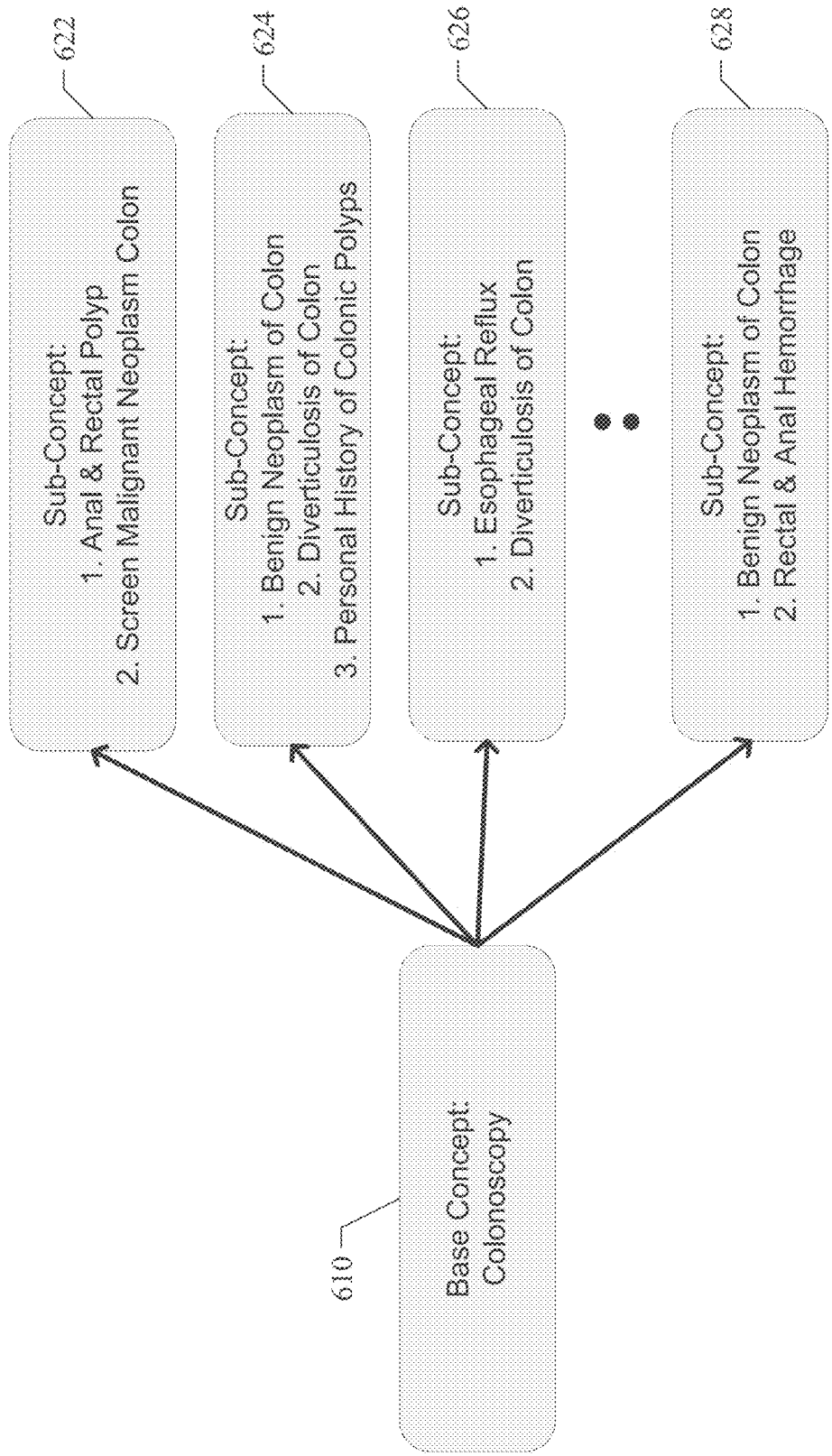
FIG. 6A illustrates an example embodiment of a performance engine comparing a base concept with one or more sub-concept groups.

FIG. 6A illustrates an example embodiment of the performance engine which considers one or more sub-concept groups 622-628 which may be associated with a base concept 610. In particular embodiments, a sub-concept group 622-628 may represent a distinct group of one or more sub-concepts, i.e. secondary conditions. In the example of FIG. 6A, sub-concept groups 624 and 628 share a common sub-concept, but differ in the other sub-concepts. In particular embodiments, several different base concepts 610 may have common sub-concepts 622-628 associated with each base concept. As an example and not by way of limitation, for multiple base concepts covering cardiovascular issues, each base concept may have similar sub-concepts corresponding to secondary conditions that will affect treatment, e.g. high blood pressure, diabetes, etc. The relationships between each base concept 610 and sub-concepts 622-628 may be stored on a data store of matching-engine system 160. As new base concept+sub-concept combinations are recorded by matching-engine system 160 (e.g. based on newly received episodes of care), the relationship data store may be updated.

Figure 6B:
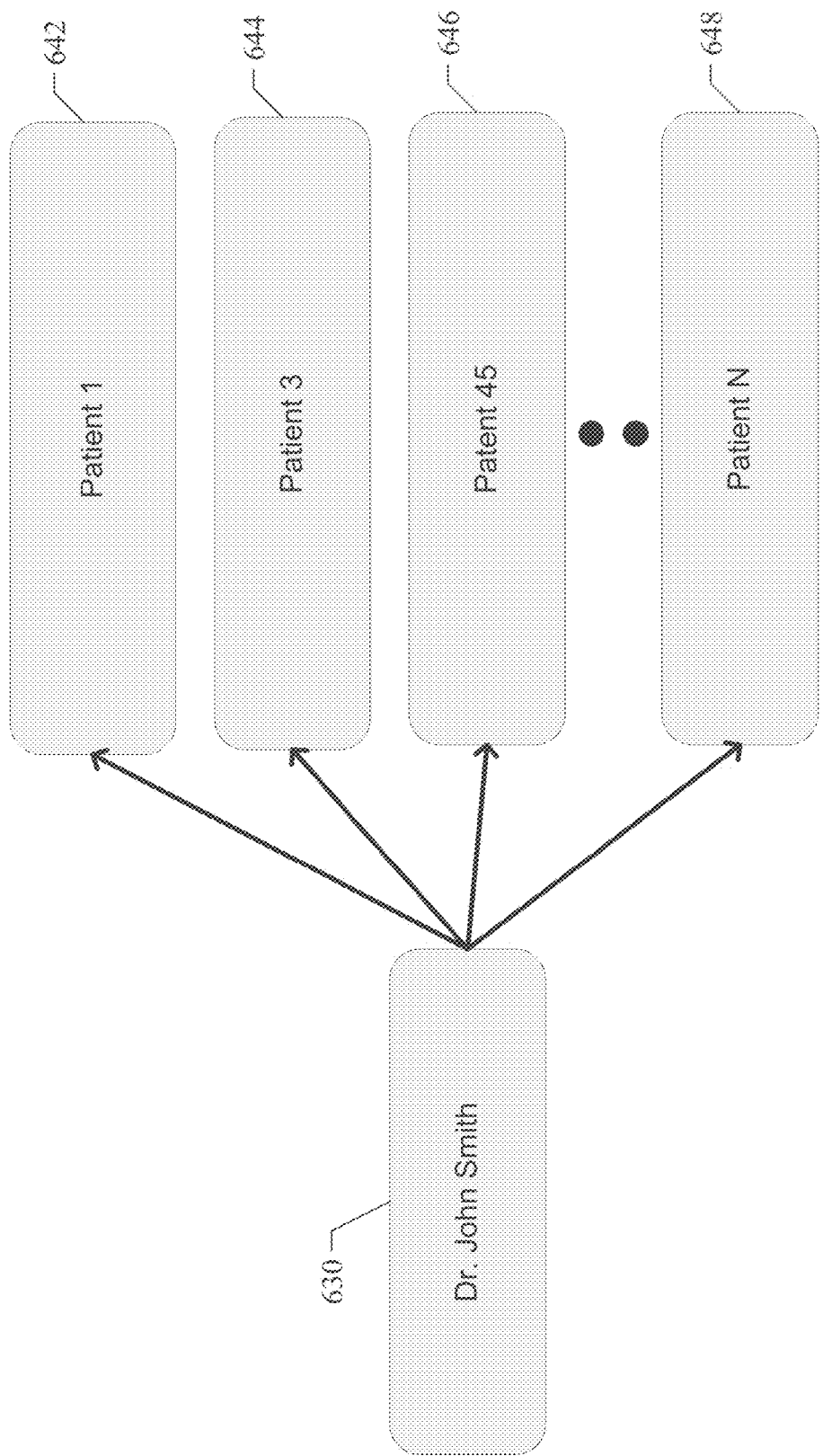
FIG. 6B illustrates an example embodiment of a performance engine matching a physician with one or more patients.

FIG. 6B illustrates an example embodiment of the performance engine which considers one or more patients 642-648 who have visited a particular physician 630 for an episode of care with base concept 610. In particular embodiments, the set of one or more patients 642-648 may represent all patients recorded for physician 630 with respect to base concept 610. In particular embodiments, matching-engine system 160 may consider a subset of patients 642-648 based on time. As an example and not by way of limitation, matching-engine system 160 may only consider patients 642-648 who have made at least one visit to physician 630 in relation to the episode of care within the last six months. In particular embodiments, as new patients come to visit physician 630 in relation to base concept 610, new patients 642-648 may be added.

Figure 6C:
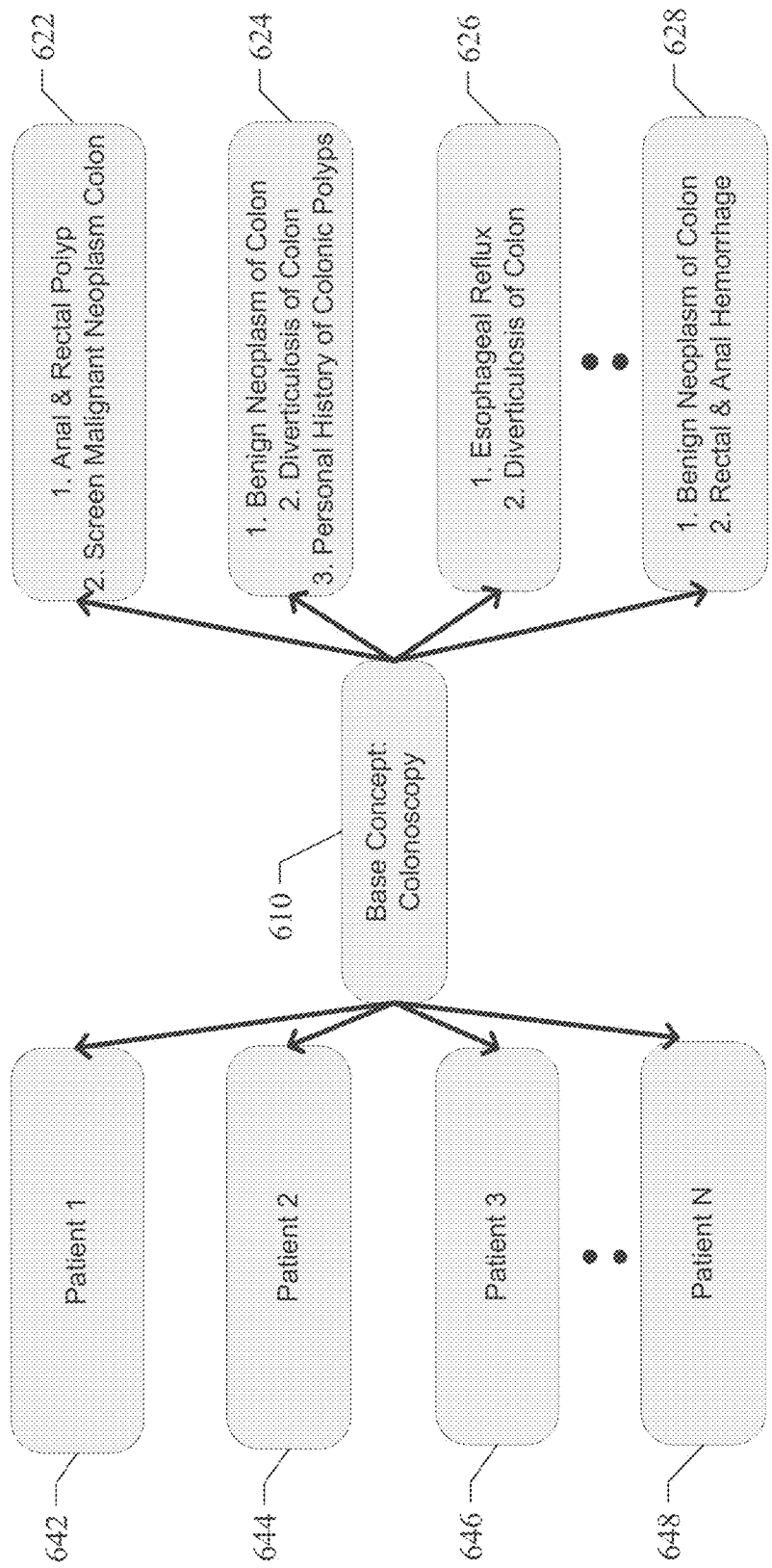
FIG. 6C illustrates an example embodiment of a performance engine matching one or more patients of a base concept with corresponding sub-concept groups.
Figure 6D:
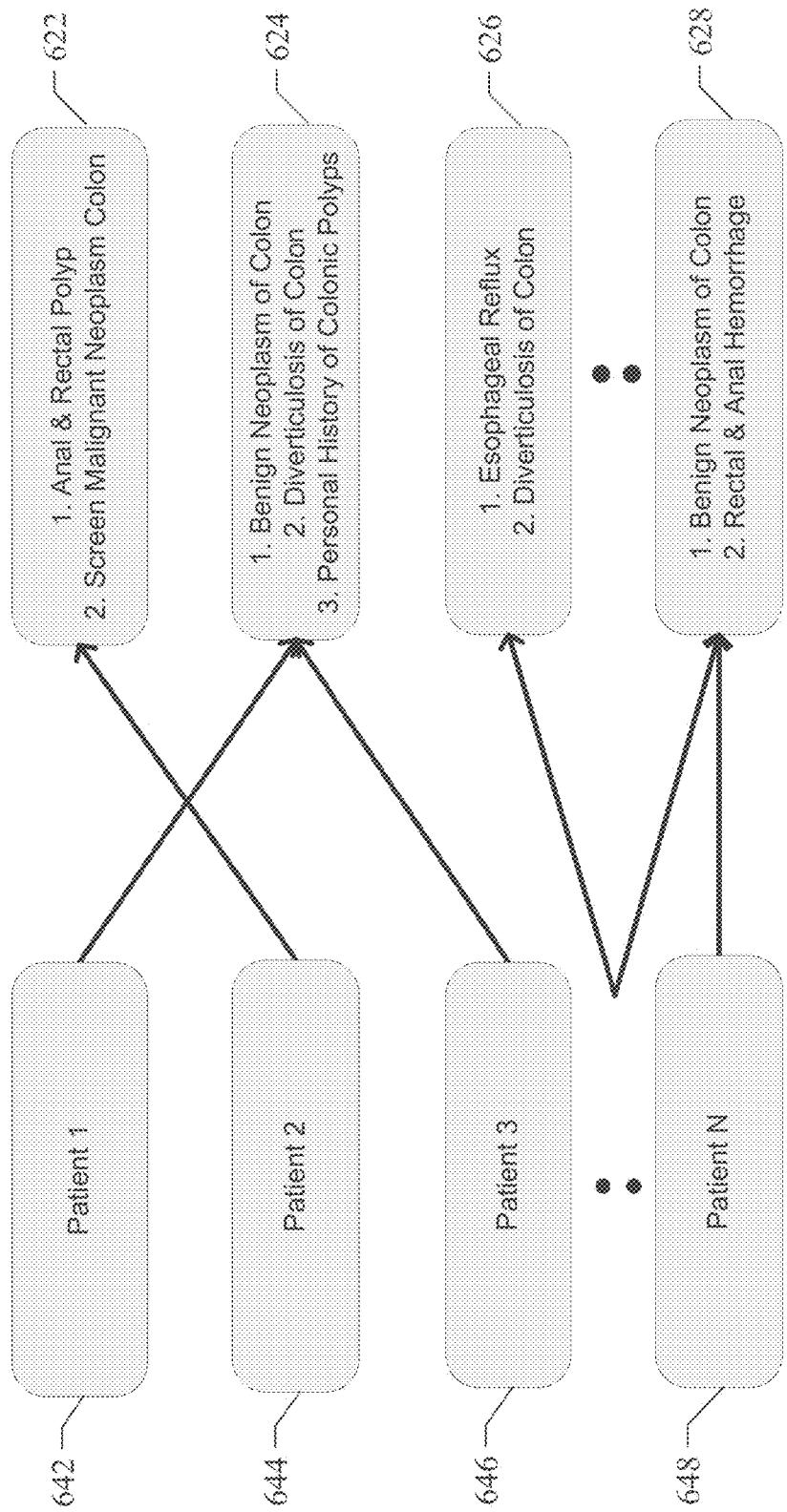
FIG. 6D illustrates an example embodiment of a performance engine matching one or more patients of a base concept with corresponding sub-concept groups.
Figure 6E:
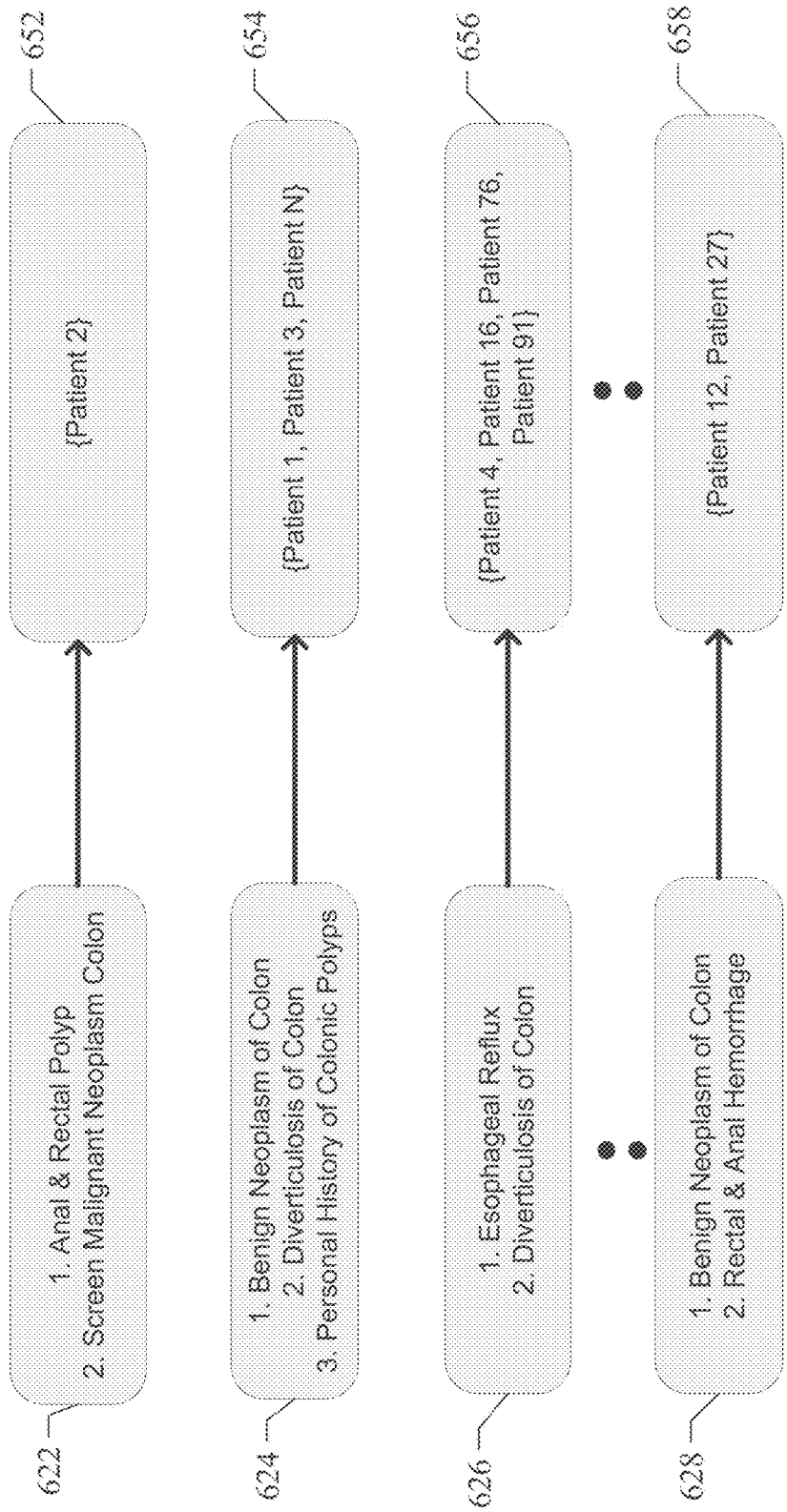
FIG. 6E illustrates an example embodiment of a performance engine matching sub-concept groups with corresponding patient groups.

FIGS. 6C, 6D, and 6E illustrate an example embodiment of the performance engine wherein each patient 642-648 is associated with one or more sub-concept groups 622-628 for the base concept 610. In particular embodiments, matching-engine system 160 may correlate a patient to the sub-concepts based on the CPT codes and ICD codes received from the health-care provider with respect to the particular patient. In particular embodiments, a physician or a health-care provider may provide an indication of one or more sub-concepts to matching-engine system 160. In particular embodiments, each patient 642-648 may be associated with a single sub-concept group 622-628, wherein each sub-concept group represents a distinct group of one or more sub-concepts, i.e. secondary conditions. In particular embodiments, each sub-concept group 622-628 may be associated with one or more patients 642-648. In the example of FIG. 6E, each sub-concept group 622-628 is associated with a patient group 652-658, wherein each patient group 652-658 comprises all patients 642-648 who have the associated sub-concept group 622-628.

Figure 6F:
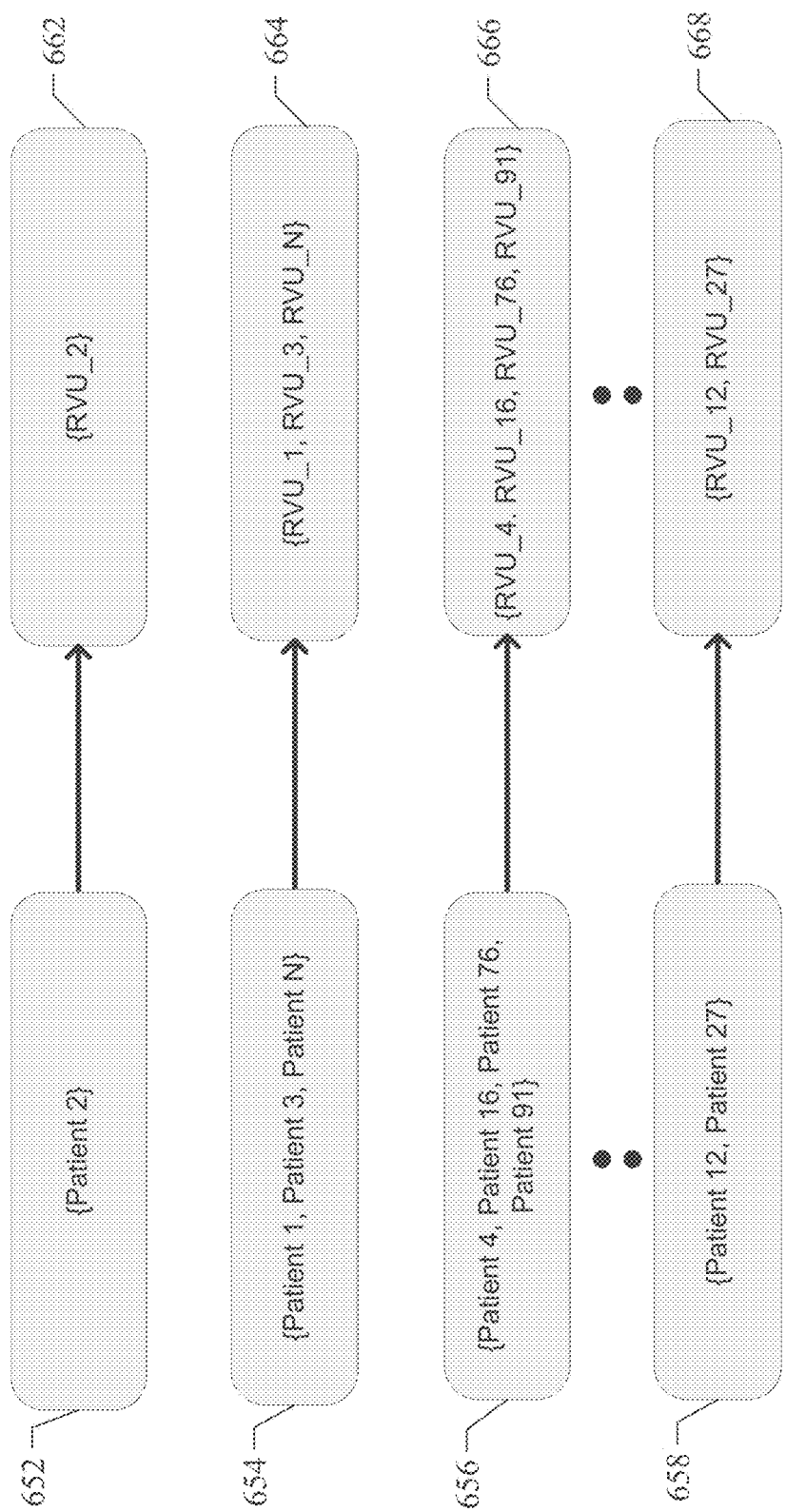
FIG. 6F illustrates an example embodiment of a performance engine matching patient groups with corresponding RVU groups.
Figure 6G:
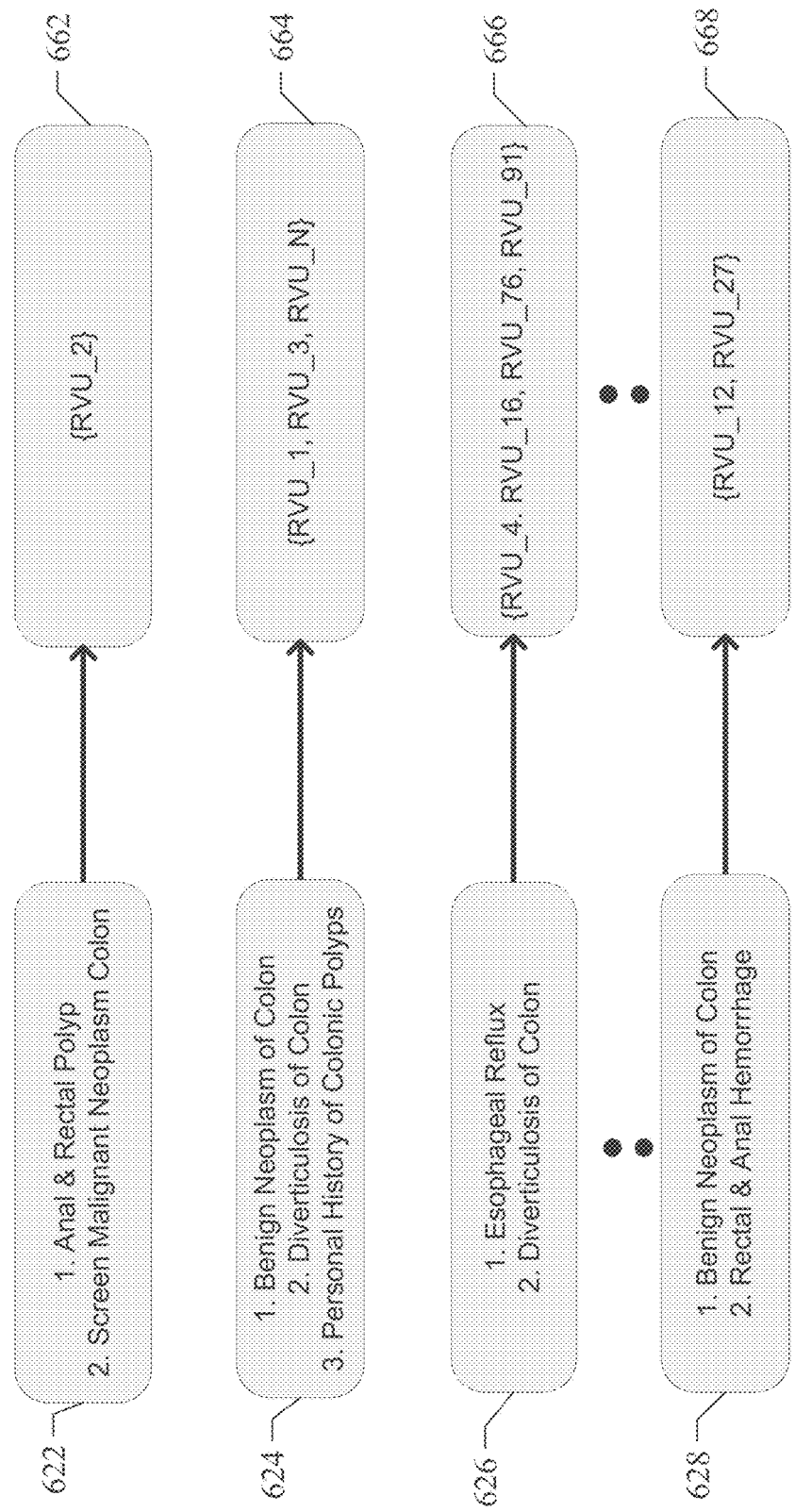
FIG. 6G illustrates an example embodiment of a performance engine matching sub-concept groups with corresponding RVU groups.

FIGS. 6F and 6G illustrate an example embodiment of the performance engine wherein the total RVU costs for each patient are averaged for each patient group 652-658 corresponding to sub-concept groups 622-628. In particular embodiments, the RVU costs for a single patient may be determined by the CPT codes sent with respect to the particular patient during the time of the episode of care. As an example and not by way of limitation, if an episode of care comprises four office visits, each visit having three CPT codes associated with them, then all twelve CPT codes associated with the episode of care may be included. In particular embodiments, as discussed above other cost factors may be included as a part of RVU, such as the actual monetary cost, non-physician services, administrative costs, or costs relating to time or number of patient visits. In the example of FIG. 6F, the total RVU costs for each patient may be included in RVU groups 662-668 corresponding to patient groups 652-658. The value for each RVU group 662-668 may represent an average value of the individual RVU costs for each patient in the group. In the example of FIG. 6G, the RVU groups 662-668 may be correlated with their respective sub-concept groups 622-628. In particular embodiments, the average RVU cost may be a weighted average, with patients seen more recently being weighted more heavily than patients seen during an earlier period of time.

Figure 6H:
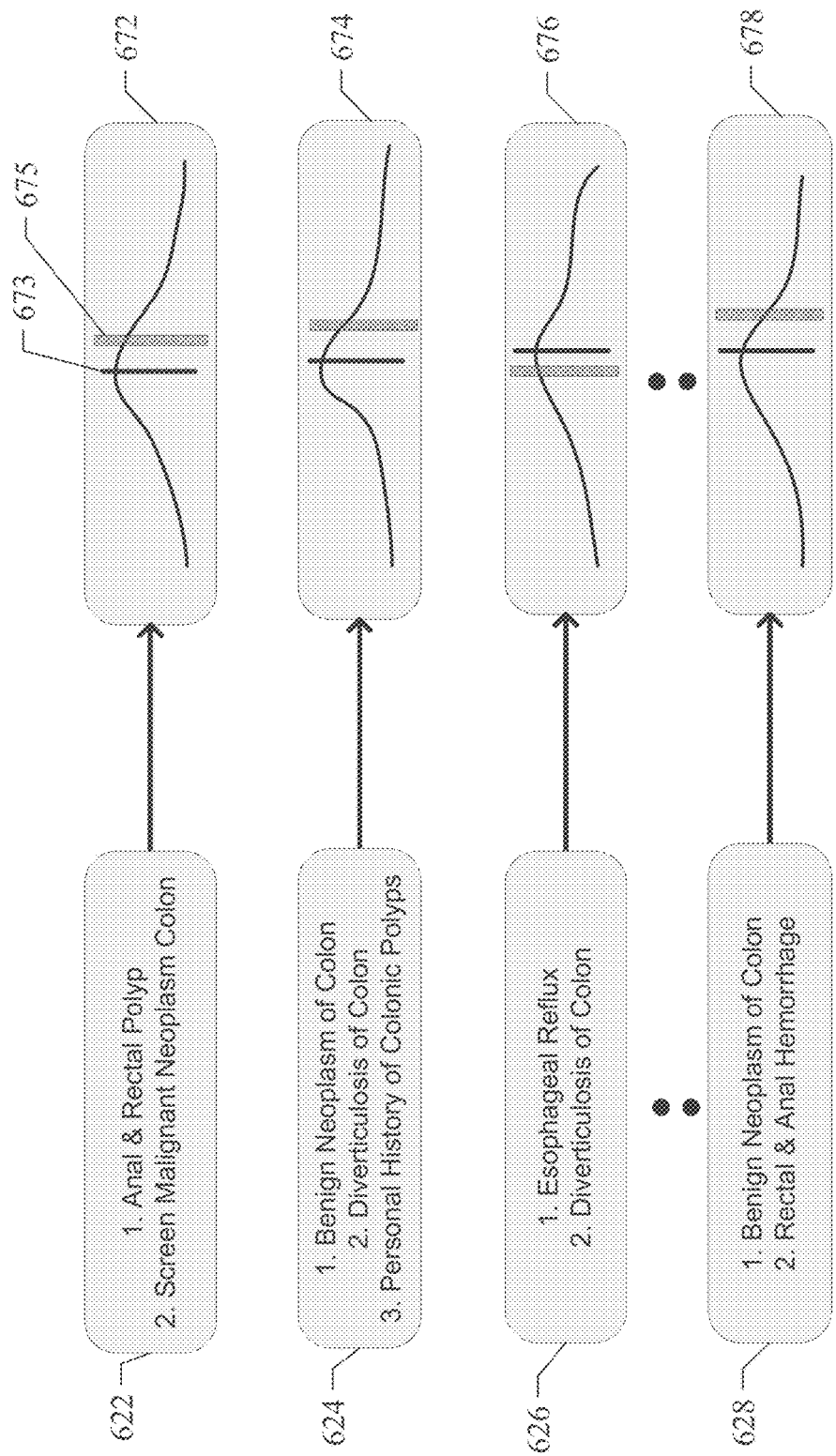
FIG. 6H illustrates an example embodiment of a physician's RVU for one or more sub-concepts compared with the distribution of RVU costs for a peer group of the physician.

FIG. 6H illustrates an example embodiment of the performance engine comparing the RVU groups for a particular physician with the RVU group costs for the peer group of physicians. As discussed above, the peer group of physicians may comprise all physicians in the same specialty and geographic region as the particular physician. In particular embodiments, matching-engine system 160 may calculate the RVU group costs 662-668 for each physician in the peer group. Based on the RVU group costs for each physician, matching-engine system 160 may calculate a distribution of RVU costs 672-678 for the peer group of physicians. The distributions 672-678 may indicate the variation in RVU costs for physicians in treating the particular base concept 610 and sub-concept groups 622-628. In particular embodiments, matching-engine system 160 may calculate the mean RVU cost for the peer group. In the example of FIG. 6H, for distribution 672, line 673 may represent the mean RVU cost for the peer group of physicians comprising distribution 672. In particular embodiments, the mean RVU cost may be weighted by the number of patients seen by each of the peer group physicians. As an example and not by way of limitation, if Dr. Paul has seen 5 patients for base concept 610 with sub-concept group 624, and Dr. Quinn has seen 50 patients for the same base concept 610 and sub-concept group 624, matching-engine system 160 may weight the average RVU cost for Dr. Quinn more greatly than the average RVU cost for Dr. Paul in determining the average RVU cost for the peer group. In particular embodiments, in order to determine the performance score for the particular physician, the average RVU cost for the particular physician may be compared against the distribution and mean of the peer group. In the example of FIG. 6H, line 675 may represent the particular physician's RVU costs for patients in that sub-concept group. In particular embodiments, the performance score may be based on the distance between the physician's RVU cost 675, and the mean RVU cost 673. In particular embodiments, the distance may be represented in units of standard deviations of the distribution 672 from the mean RVU cost 673. In particular embodiments, if a particular physician's individual RVU is more efficient (e.g. lower-cost) than the peer group, the performance score may be positive; if the individual RVU is less efficient (higher costs), then the performance score may be a negative value.

In particular embodiments, matching-engine system 160 may then determine a set of performance scores for each sub-concept group 622-628, wherein each performance score corresponds to the difference between the particular physician's RVU costs within the sub-concept group, compared to the average RVU costs of the peer group. In particular embodiments, matching-engine system 160 may then aggregate the individual performance scores into a total performance score for a particular base concept 610. In particular embodiments, matching-engine system 160 may weight each performance score based on the number of patients the particular physician has treated with the underlying sub-concept group. The aggregate performance score may then be calculated as a weighted average. As an example and not by way of limitation, if Dr. Tina has a performance score of 0.5 in sub-concept group 622 with ten patients seen, and has a performance score of 2.5 in sub-concept group 624 with twenty patients seen, then matching-engine system 160 may calculate the aggregate performance score to be ((0.5*10)+(2.5*20))/30=2.00.

In particular embodiments, matching-engine system 160 may calculate a weighted average for the aggregate performance score based on the number of patients seen by the peer group of physicians for each sub-concept type. This may reflect the overall likelihood that a user seeking a physician within the base concept has a particular sub-concept type. As an example and not by way of limitation, matching-engine system 160 may determine in the example above that a total of 100 patients were treated by physicians in Dr. Tina's peer group with sub-concept group 622, and a total of 50 patients were treated with sub-concept group 624. In this example, if a new user is seeking treatment for the same base concept, matching-engine system 160 may determine that a user is twice as likely to have sub-concept group 622 as 624. The weighted average aggregate performance score in this example for Dr. Tina may then be ((0.5*100)+(2.5*50))/150=1.167.

Experience Index

In particular embodiments, matching-engine system 160 may consider the experience index of physicians in generating or ranking the set of physicians for recommendation to the user. An experience index may represent the overall experience of a physician in dealing with a particular type of conditions or diseases, beyond a mere count of patients who have visited the physician. In particular embodiments, an experience index may also account for relative case volume, case severity, and variety seen by the physician. In particular embodiments, the experience index may be localized to be evaluated against physicians within a given state; within a given MSA; within a specialty class within the MSA; within a specialization within the specialty class; and within a condition group within the specialization based on diagnoses and procedure codes. In particular embodiments, using a localized context for the experience index may allow for a very homogenous context of analysis, may allow for environmental and population health factors to be included in the analysis, and may narrow the context of the analysis. The experience index is calculated using only provider-reported insurance claims data, and thus will be free of any subjective reviews from patients. Another advantage to the experience index may be that because it is calculated by comparing providers to each other, just two providers in the same specialization in the same locality are needed to calculate the experience index.

Figure 7:
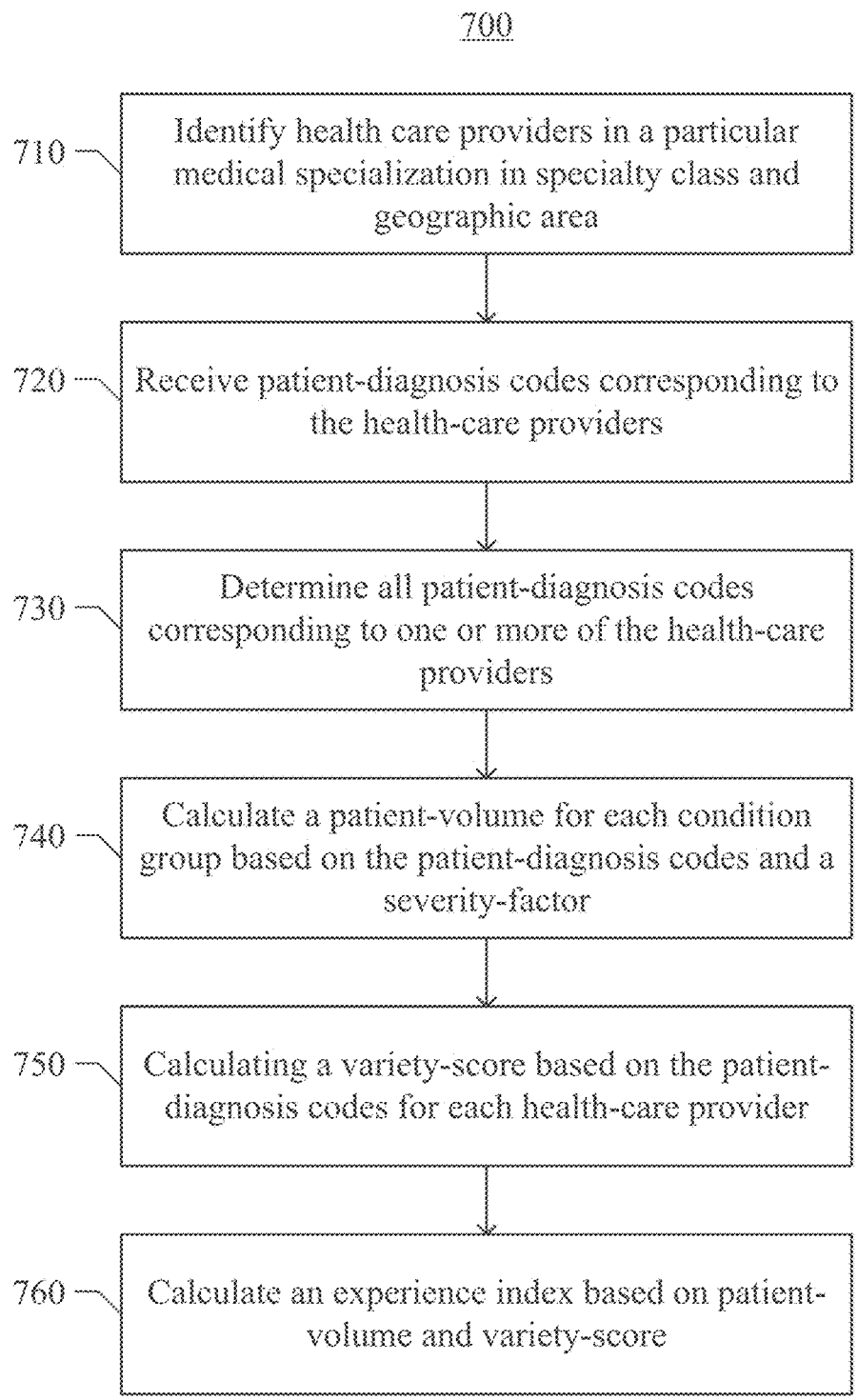
FIG. 7 illustrates an example method of calculating an experience index for a physician.

FIG. 7 illustrates an example method of calculating an experience index for a particular physician. The method may begin at step 710, where matching-engine system 160 may identify all health-care providers or physicians within a particular specialization in a specialty class and geographic area. As an example and not by way of limitation, a specialization may be cardiology within a specialty class of internal medicine. In particular embodiments, the geographic area may be an MSA within a particular state. At step 720, matching-engine system 160 may receive patient-diagnosis codes corresponding to the identified health-care providers. As an example and not by way of limitation, patient-diagnosis codes may comprise ICD codes submitted by the providers on insurance claims. In particular embodiments, the patient-diagnosis codes may correspond to one or more condition groups. Each condition group may represent a similar group of conditions or diseases. At step 730, matching-engine system 160 may determine all patient-diagnosis codes corresponding to one or more of the providers. In particular embodiments, this step may comprise determining all patient-diagnosis codes within a particular condition group for a provider. In particular embodiments, each patient-diagnosis code received by matching-engine system 160 may further comprise a severity index which represents whether the underlying instance of the condition for the patient-diagnosis code was non-chronic or chronic.

At step 740, matching-engine system 160 may calculate a patient-volume for a particular condition group for a provider based on the received patient-diagnosis codes and the corresponding severity factors. In particular embodiments, the volume of patients may be a relative measure of how many patients a particular provider saw compared to the rest of the identified providers. As an example and not by way of limitation, in a condition group for cardiac dysrhythmias, a total group of providers may have seen 100 patients with chronic cases, and 200 patients with non-chronic cases. Within the group of providers, Dr. Alex may have seen 20 of the chronic cases, and 30 of the non-chronic cases. In this example, the case volume for Dr. Alex would be 20/100=0.20 for chronic cases of cardiac dysrhythmia, and 30/200=0.15 for non-chronic cases. The two case volumes may be combined by adjusting for case severity. In particular embodiments, chronic cases may be multiplied by an additional factor. As an example and not by way of limitation, chronic cases may be deemed to require three times as many resources as non-chronic cases. Therefore, chronic case volume may be weighted three times as much as non-chronic cases. In the example above, Dr. Alex may have a severity-normalized case volume of (0.20*3+0.15)/(3+1) =0.1875. A higher normalized case volume may indicate that the particular provider has seen more overall cases in the condition group, and/or more severe cases compared to their peers.

At step 750, matching-engine system 160 may also calculate a variety score for the group of health-care providers. In particular embodiments, the variety score may represent the number of types of diseases seen by a particular provider within a specialization. Matching-engine system 160 may determine a total variety of conditions by determining the number of distinct patient-diagnosis codes submitted by all identified providers within a specialization. As an example and not by way of limitation, matching-engine system 160 may receive fifty different patient-diagnosis codes from cardiologists within the Denver, Colo. MSA. Using only the distinct conditions seen within the geographic region may adjust the variety for the population health, e.g. if no one in the MSA has a particular condition within the condition group. Matching-engine system 160 may then determine the number of distinct patient-diagnosis codes seen by a particular provider. In this example, if Dr. Jones, a cardiologists from Denver, has seen forty distinct conditions with their own patient-diagnosis codes, matching-engine system 160 may determine that Dr. Jones' variety score is 40/50=0.8. In particular embodiments, the variety score may be calculated based on the number of condition groups within a specialization are seen by one provider versus the entire group of providers.

At step 760, matching-engine system 160 may calculate an experience index based on the severity-normalized case volume and the variety score. In particular embodiments, the experience index may be the product of the severity-normalized case volume and the variety score. In particular embodiments, the experience index may be a weighted sum or average of the severity-normalized case volume and the variety score. As an example and not by way of limitation, a weighted average may be used if matching-engine system 160 determines that the normalized case volume is more indicative of a physician's experience than the variety of cases the physician has seen.

Particular embodiments may repeat one or more steps of the method of FIG. 7, where appropriate. Although this disclosure describes and illustrates particular steps of the method of FIG. 7 as occurring in a particular order, this disclosure contemplates any suitable steps of the method of FIG. 7 occurring in any suitable order. Moreover, although this disclosure describes and illustrates particular components, devices, or systems carrying out particular steps of the method of FIG. 7, this disclosure contemplates any suitable combination of any suitable components, devices, or systems carrying out any suitable steps of the method of FIG. 7.

Figure 8A:
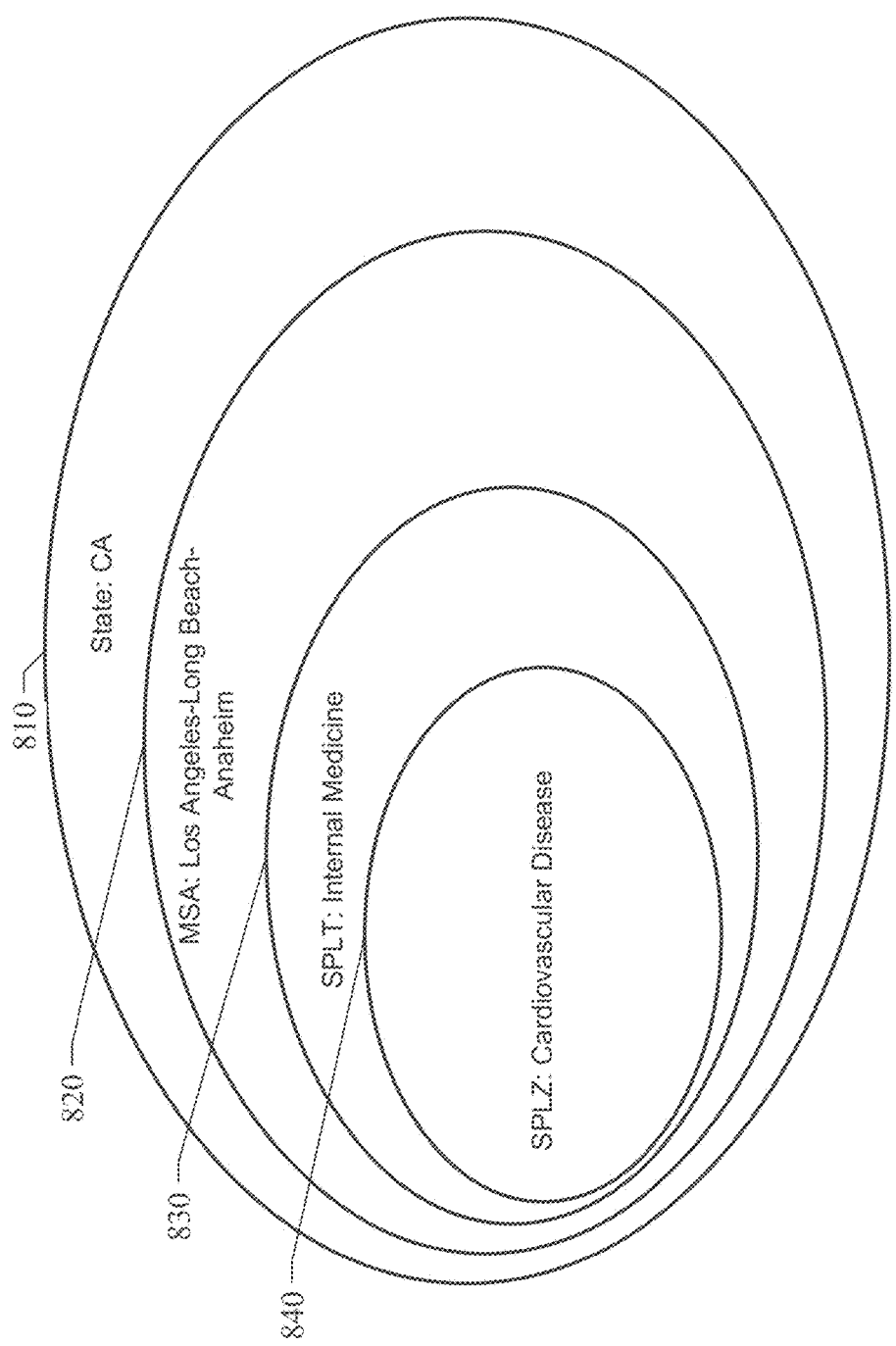
FIG. 8A illustrates an example embodiments of an experience engine determining a group of physicians based on specialization and geographic area.
Figure 8B:
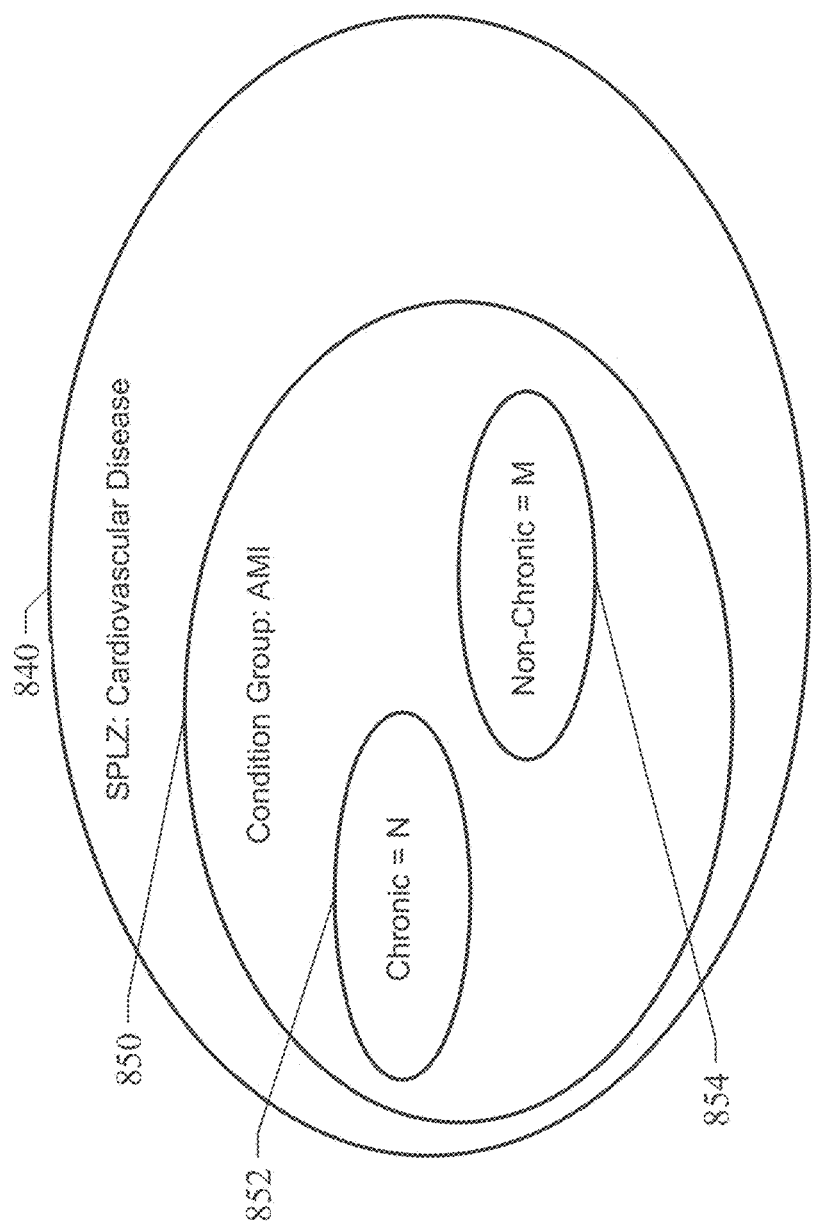
FIG. 8B illustrates an example embodiment of an experience engine determining a case volume for a particular specialization.

FIGS. 8A-8B illustrate example embodiments of the experience engine of matching-engine system 160. In the example of FIG. 8A, matching-engine system 160 may identify health-care providers or physicians within a particular specialization 840, within a particular specialty class 830, within a particular metropolitan statistical area (MSA) 820 within a state 810. The providers belonging to this narrowed group of specialists by specialization 840 may comprise a peer group of providers to determine the relative case volume and case variety for one of the providers. In the example of FIG. 8B, the number of cases within a particular condition group 850 may be identified within the specialization 840. Within condition group 850, matching-engine system 160 may identify a number of chronic cases 852, as well as a number of non-chronic cases 854. In particular embodiments, the number of cases 852 and 854 may be for a specific provider within specialization 840. In particular embodiments, the number of cases 852 and 854 may be for all providers within specialization 840. As discussed above, the ratio of cases seen by one provider may be compared to the number of cases seen by all providers to calculate a relative case volume, which may be normalized by case severity.

Figure 8C:
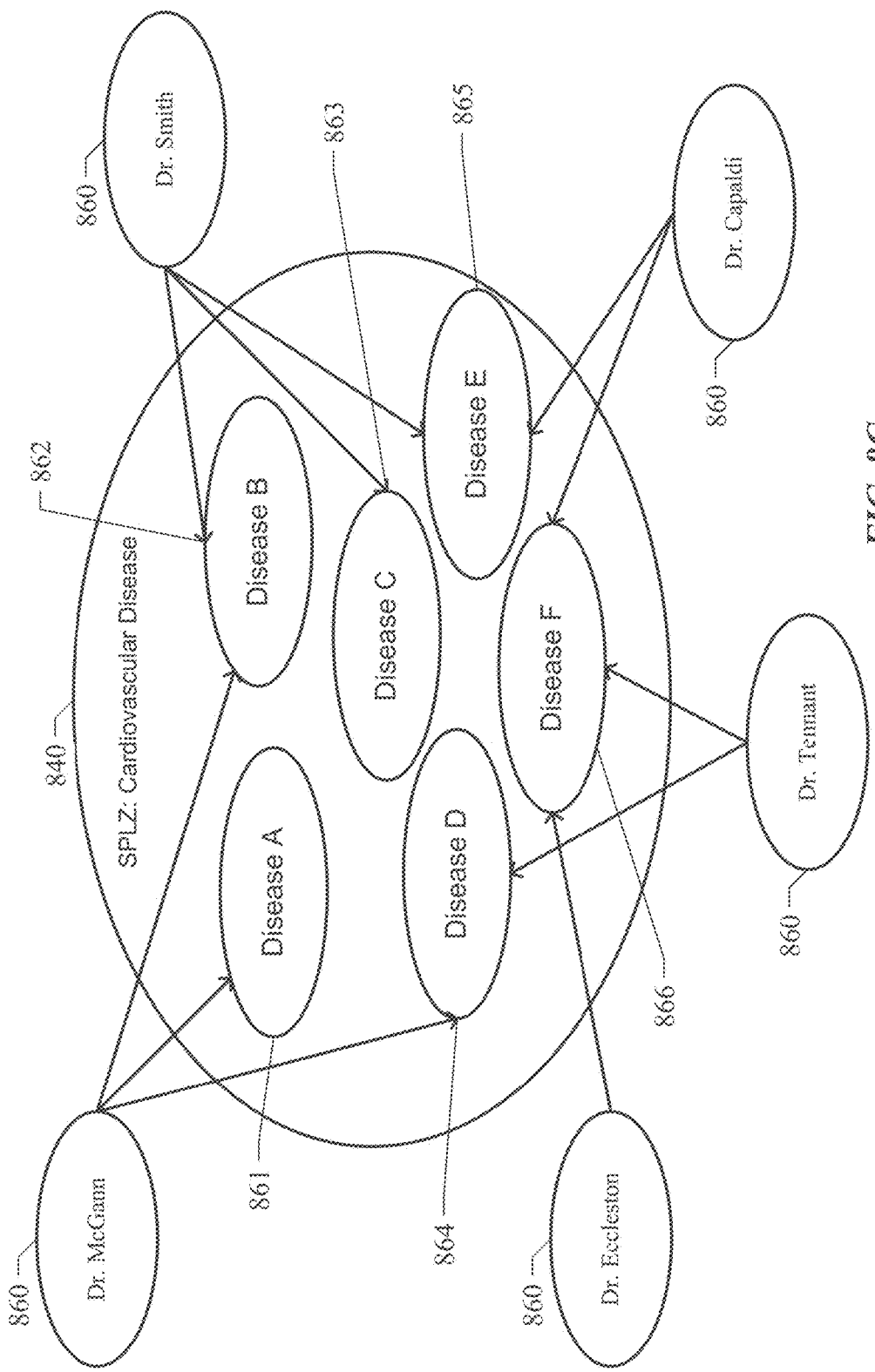
FIG. 8C illustrates an example embodiment of an experience engine determining a variety-score for physicians in a specialization.

FIG. 8C illustrates an example embodiment of determining a variety score. In this example, specialization 840 may comprise five physicians 860. Over a predetermined period of time, these physicians 860 may have diagnosed patients with six distinct conditions 861-866. Each of the conditions 861-866 may comprise a different condition group; or matching-engine system 160 may calculate variety based on distinct conditions within a condition group. Matching-engine system 160 may compare the number of conditions seen by each physician versus the total number of conditions seen by the group. In the example of FIG. 8C, Dr. McGann has seen three conditions; Dr. Eccleston has seen one; Dr. Tennant has seen two; Dr. Capaldi has seen two; and Dr. Smith has seen three. Matching-engine system 160 may divide each of these numbers by the total number of conditions for this specialization 840 to obtain variety scores for the five doctors: Dr. McGann and Dr. Smith have variety scores of 0.5; Dr. Eccleston has 0.167; and Dr. Tennant and Dr. Capaldi have variety scores of 0.33. Matching-engine system 160 may use these variety scores in combination with a severity-normalized case volume for each provider to determine the overall experience index.

User Interface

Figure 9:
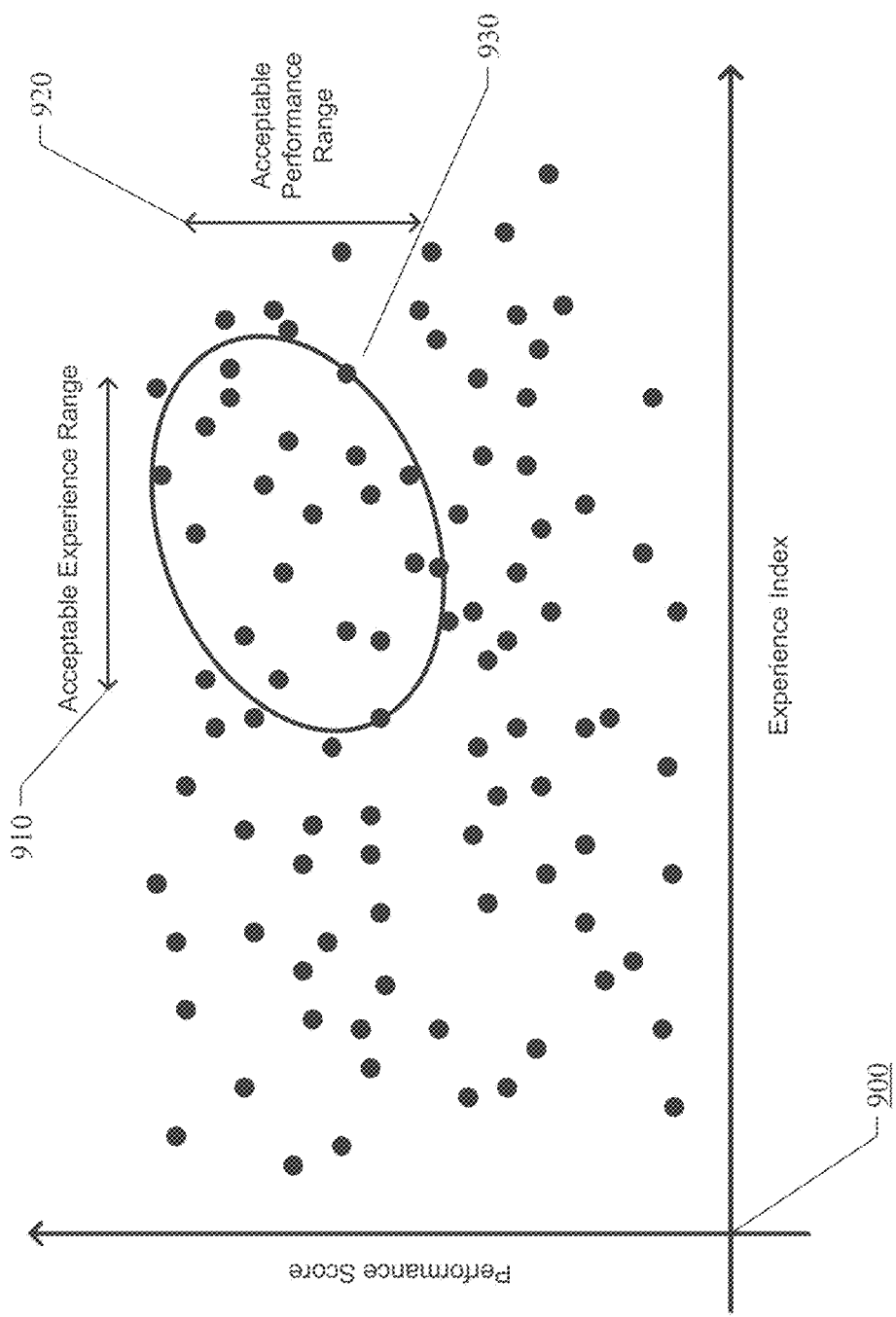
FIG. 9 illustrates an example embodiment of the matching engine selecting a set of physicians based on parameters for performance scores and experience indices.

In particular embodiments, the performance scores and experience index for each physician may be used to determine whether the physician should be recommended to a particular user based on a request sent by that user. FIG. 9 illustrates an example embodiment for selecting one or more physicians for recommendation. Graph 900 show examples of physicians plotted by their respective experience indices and performance scores. In particular embodiments, a single graph like graph 900 may only show the plotted experience indices and performance scores for a particular base-concept. In the example of FIG. 9, graph 900 includes acceptable ranges 910 and 920 for the performance score and experience index, respectively. Acceptable ranges 910 and 920 create a region 930 of data points which are acceptable for recommendation to a user. Matching-engine system 160 may determine that physicians with data points within region 930 are acceptable for recommendation to the user.

Figure 10A:
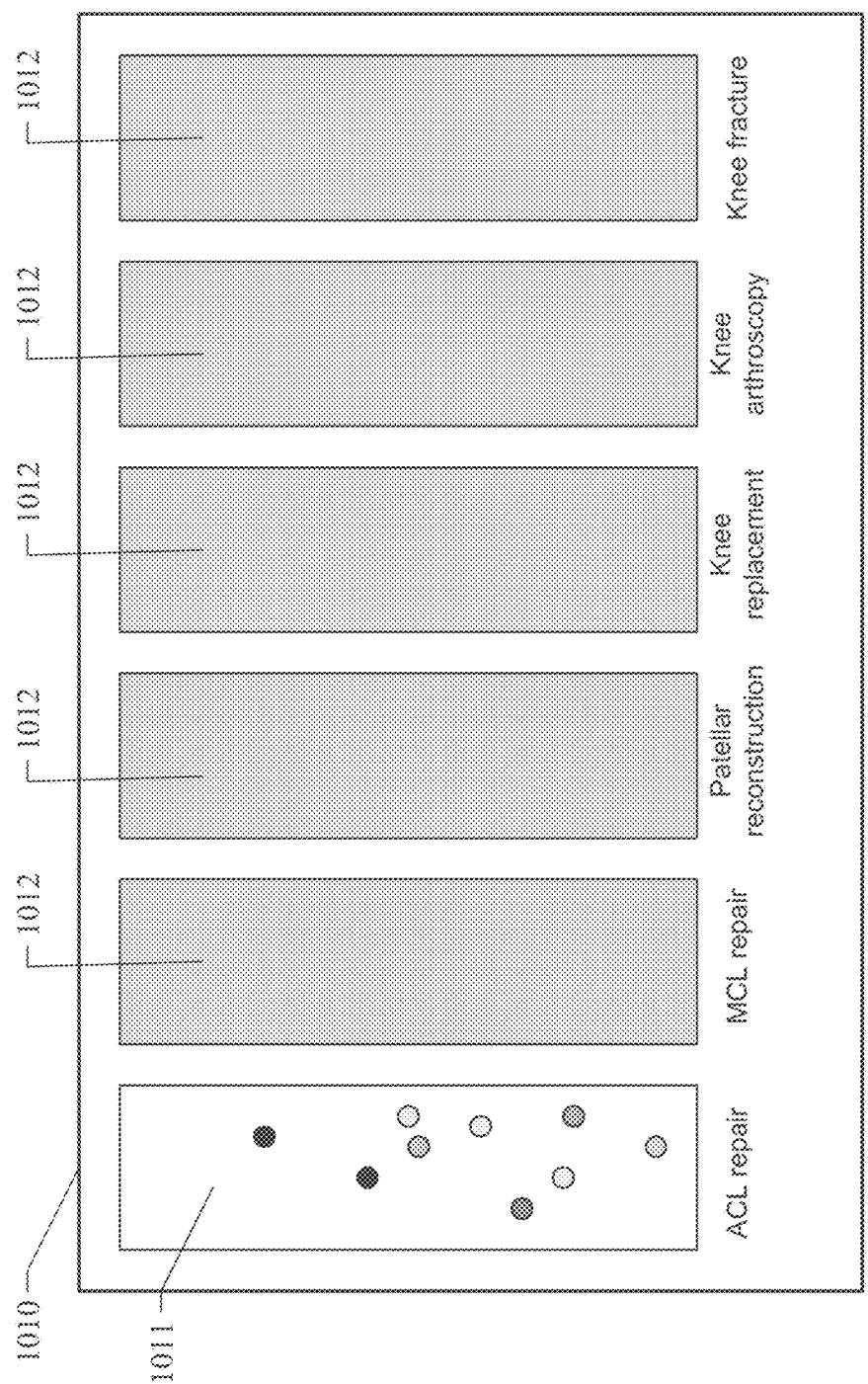

In particular embodiments, one or more physicians or health-care providers may be recommended to a user submitting a search query. FIG. 10A illustrates an example user-interface 1010 for presenting a set of physicians to the user. In the example of FIG. 10A, a user may be presented with treatment types 1011 and 1012, wherein each treatment type corresponds to a particular treatment, medical condition, or condition-group. The treatment types 1011 and 1012 in the example of FIG. 10A correspond to various types of treatments involving the knee, or a condition regarding the knee. For example, these categories may be presented to a user who input "sharp knee pain." As another example, the user may have specifically searched for "ACL repair," and the other treatment types 1012 may be presented as related searches or categories. The user may interact with treatment types 1011 and 1012 to view more information within the selected treatment type.

Figure 10B:
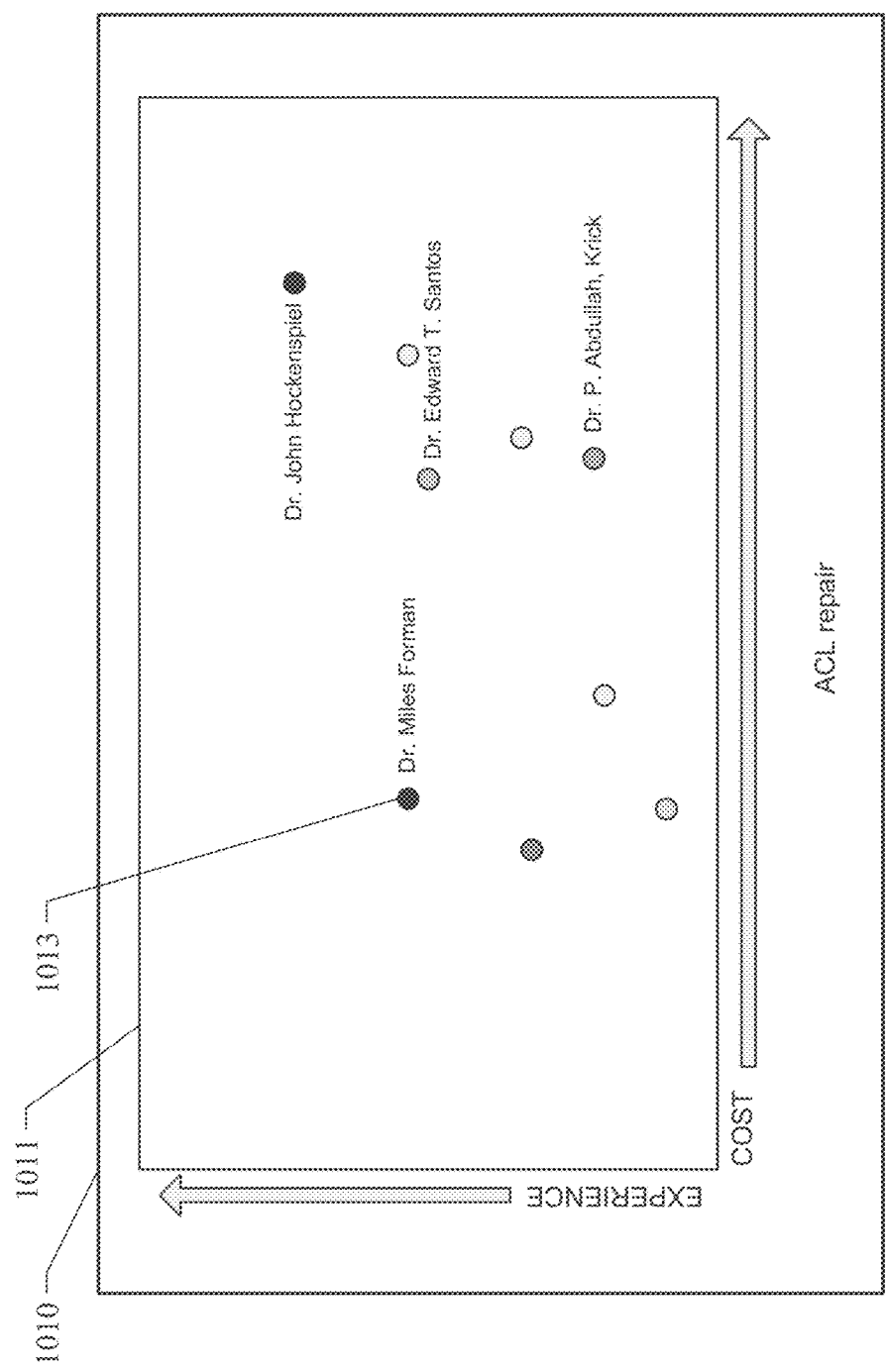
Figure 10C:
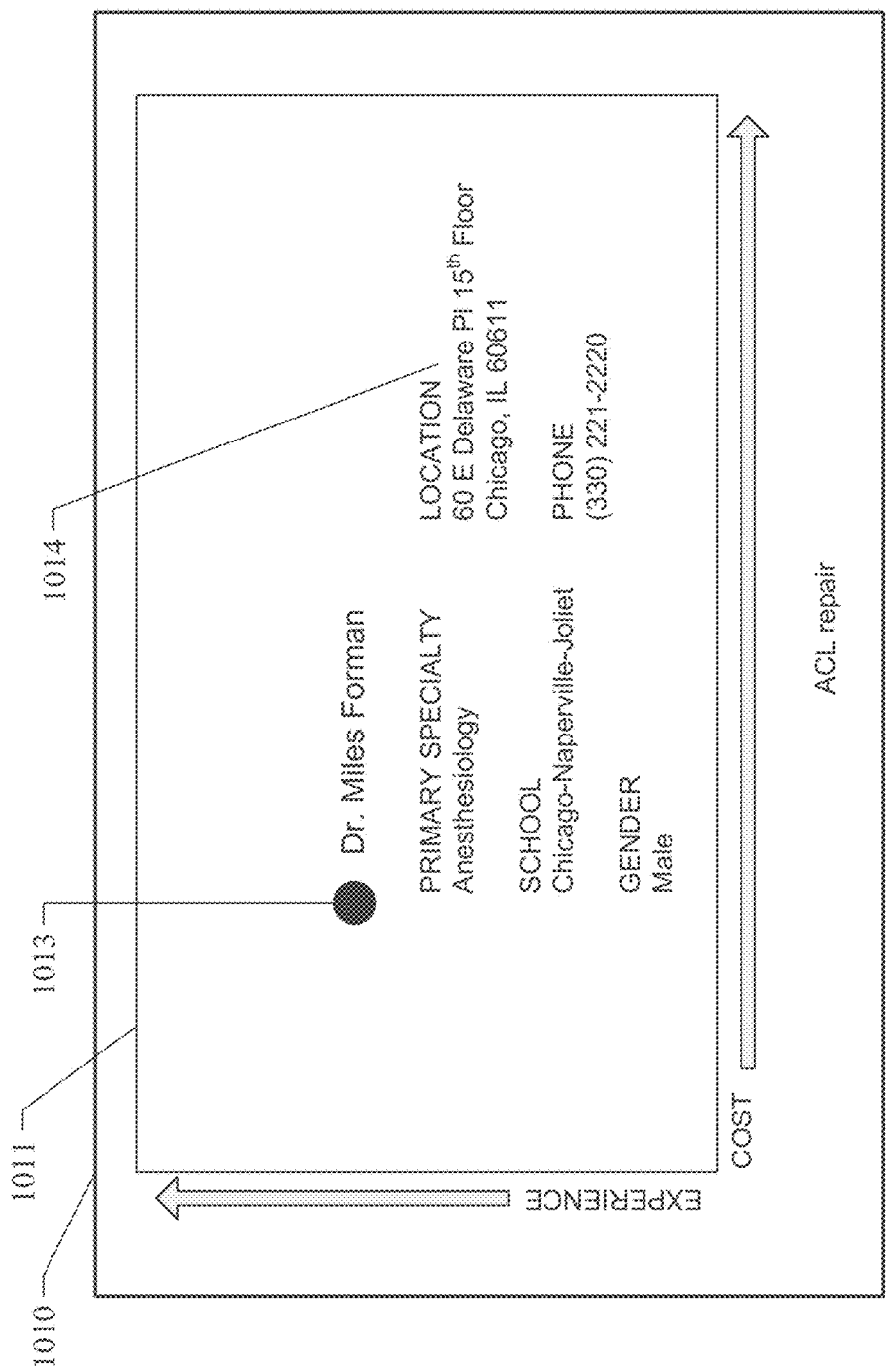

FIG. 10B illustrates an embodiment of the user-interface 1010 of FIG. 10A once treatment type 1011 has been selected by the user. Treatment type 1011 may be expanded to a full graph, wherein the axes of the graph correspond to a cost value of the physician, and the experience of the physician. In particular embodiments, the cost value may correlate to the performance score of the physician. In particular embodiments, the cost value may correlate to the monetary costs corresponding to each physician for services related to treatment type 1011. Each physician 1013 may be represented as a point on the graph, wherein each point's x and y values correspond to the physician's cost value and experience. In particular embodiments, each physician point 1013 may be represented by a shaded region, wherein the intensity of the shading corresponds to the strength of the recommendation. As an example and not by way of limitation, in FIG. 10B, point 1013 corresponding to Dr. Miles Forman is shaded black, which may indicate that Dr. Forman is strongly recommended. Other physician points with lighter shading may correspond to physicians that are not as strongly recommended to the user. In particular embodiments, a user may interact with physician point 1013 to view further information about the physician. FIG. 10C illustrates an example embodiment of user-interface 1010 once a physician point 1013 has been selected. In the example of FIG. 10C, additional physician information 1014 may be presented to the user. In particular embodiments, physician information 1014 may comprise data reflecting reasons why the physician was recommended, such as quantitative measures of experience, cost, or distance from the user.

FIG. 10D illustrates an example embodiment of a user-interface 1020 for presenting recommended physicians in a list 1021. In the example of FIG. 10D, a user may view additional information for each physician, and sort the list 1021 by a column 1022. As an example and not by way of limitation, the example of FIG. 10D shows a list 1021 sorted by the number of procedures performed by each physician in column 1022. In particular embodiments, the columns 1022 may display information that is not a corresponding value to the experience index or performance score of the physician. As an example and not by way of limitation, users may not instinctively grasp values such as experience indices or performance scores, but may understand concepts such as "number of procedures performed" and "duration of care." In particular embodiments, the experience index and performance score may be presented in an easily-understood form. As an example and not by way of limitation, in FIG. 10D, the experience index may correspond to the column for "experience vs peers," which only has values for "most," "more," "average," and "less." As another example, the performance score may correspond to the column for "cost vs peers," which is represented by a number of dollar signs.

Figure 10E:
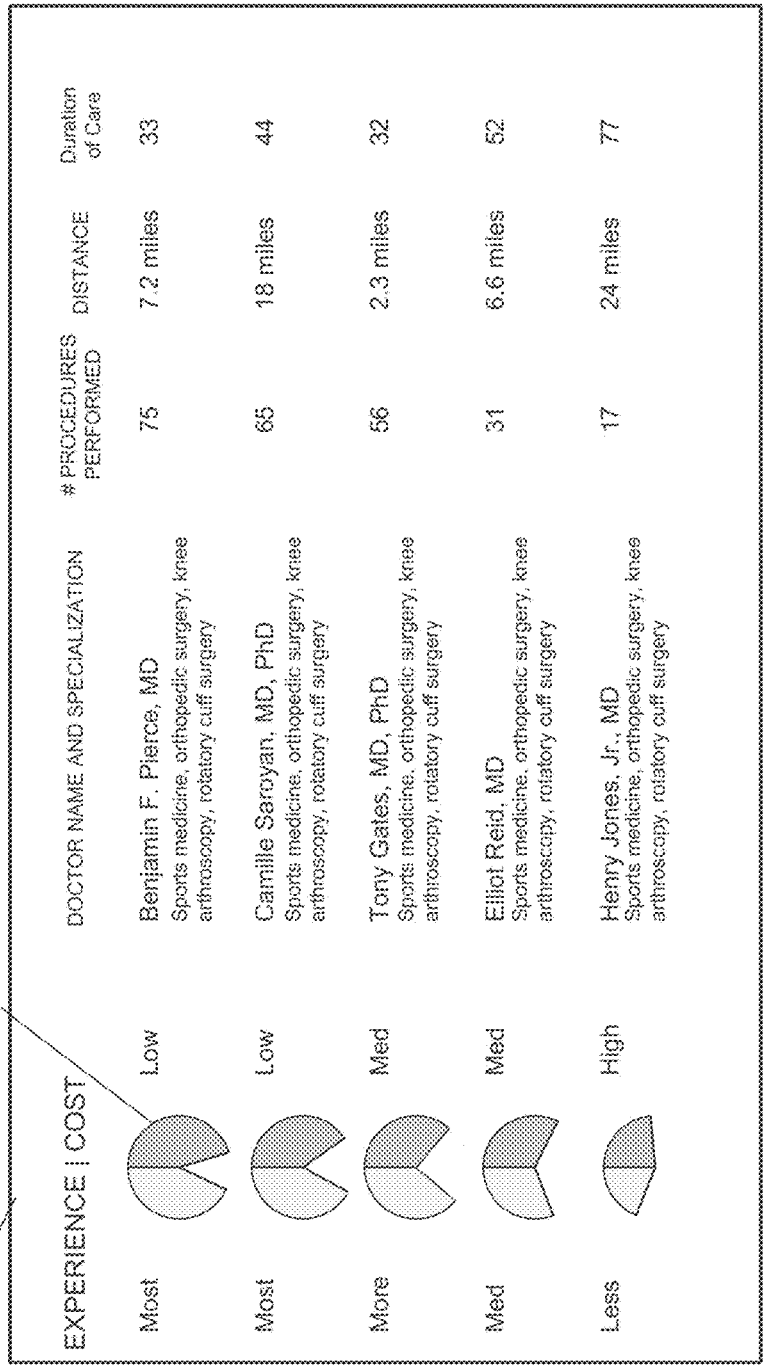

FIG. 10E illustrates another example embodiment of a user-interface 1030 for presenting recommended physicians. User-interface 1030 displays information substantively identical to user-interface 1020 of FIG. 10D. In the example of FIG. 10E, user-interface 1030 displays the experience of the physician and relative cost in a pie chart format 1031. In this example, more complete sections of the pie chart may correspond to better values for experience and cost.

Referral Network

In particular embodiments, matching-engine system 160 may be able to monitor referrals made by a first physician to a second physician. A first physician may refer a patient to a second physician for further medical services, for example services that are not within the first physician's specialty or a service that the first physician feels the second physician may perform better for the patient. As an example and not by way of limitation, if an internal medicine specialist is treating a patient and diagnoses that the patient has a heart murmur, the internist may refer the patient to a cardiologist for further diagnosis or treatment. The internist may recommend any cardiologist, or may recommend one by name to the patient.

In particular embodiments, matching-engine system 160 may comprise a physician-referral-network which records existing and new referrals made between physicians of the physician-referral-network. In particular embodiments, the physician-referral network may comprise a plurality of nodes and a plurality of edges connecting the nodes, wherein each node corresponds to a physician, and an edge connecting two physician-nodes indicates at least one direct referral between the physicians. In particular embodiments, the edges may comprise information referencing a number of referrals made in either direction between two physicians, and what types of medical services are referenced in the referrals. In particular embodiments, information pertaining to the number and type of referrals may be stored with each node.

Figure 11:
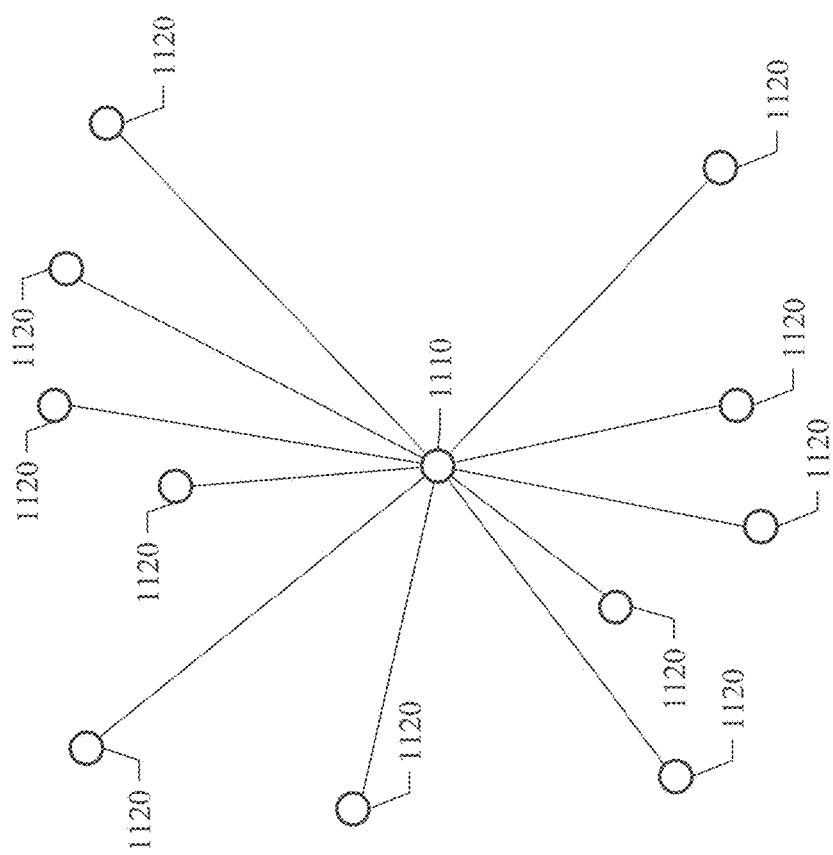
FIG. 11 illustrates an example embodiment of a physician-referral-network.

FIG. 11 illustrates an example embodiment of a physician-referral-network for matching-engine system 160. Node 1110 corresponding to a first physician is connected by a plurality of edges with a plurality of nodes 1120 corresponding to a plurality of second physicians. In particular embodiments, one edge may be used for referrals from the first physician to a second physician, and a separate edge may be used for referrals in the other direction, e.g. from the second physician back to the first physician. In particular embodiments, the same edge may be used for referrals in both directions. In particular embodiments, matching-engine system 160 may only maintain edges for physicians within the same geographic location, such as an MSA. As an example and not by way of limitation, a physician may refer a patient to another physician across the country. This may be because the referred physician is renowned as the best in the field, or because the patient is traveling or moving to the location of the other physician. Matching-engine system 160 may consider these types of referrals to be an outlier referral, and not include the referral in the physician-referral-network. In particular embodiments, matching-engine system 160 may record any and all referrals made between healthcare providers, regardless of location or specialties.

In particular embodiments, the physician-referral-network may be used to identify unnecessary referrals. As an example and not by way of limitation, a particular physician may have a habit of referring patients to another physician for tests which are unnecessary for the patient's condition or treatment. In particular embodiments, the referring physician may simply be inefficient in making the referral. In particular embodiments, the referring physician may be intentionally making unnecessary referrals to drive up claims. Matching-engine system 160 may be able to determine that a referral from a first physician to a second physician tends to result in very low performance scores for one or both physicians, indicating that the referral results in inefficient treatment. Matching-engine system 160 may also be able to identify whether a first physician is making a referral to a second physician who is below-average experience in the type of medical services that the referral comprises, particularly if compared to other physicians referred to by the first physician or the first physician's peers. In particular embodiments, matching-engine system 160 may use a threshold performance score or experience index for referred physicians with respect to a referring physician.

In particular embodiments, matching-engine system 160 may inform either the referring physician or referred physician, or both, that the referrals are inefficient. As an example and not by way of limitation, matching-engine system 160 may be able to inform a physician who always refers patients for a particular condition that the referral is unnecessary for treatment or is an inefficient use of resources. In particular embodiments, if a referring physician makes referrals to another physician with resulting performance scores below the threshold performance score, matching-engine system 160 may filter out that referring physician from a set of recommended physicians for users requesting treatment in the same base concept or specialization as the unnecessary referrals. As an example and not by way of limitation, a referring physician Dr. Grant may see patients with migraines and/or vertigo. Dr. Grant may refer his migraine patients to Dr. Sattler, and refer his vertigo patients to Dr. Harding. However, if the performance score for patients referred to Dr. Harding fall below a threshold score, indicating that the referral may be unnecessary, matching-engine system 160 may filter out Dr. Grant from the set of recommended physicians for users searching for vertigo treatments. If the performance scores for patients referred to Dr. Sattler remain above a threshold, matching-engine system 160 may keep recommending Dr. Grant for users looking for physicians to treat migraines.

Figure 12:
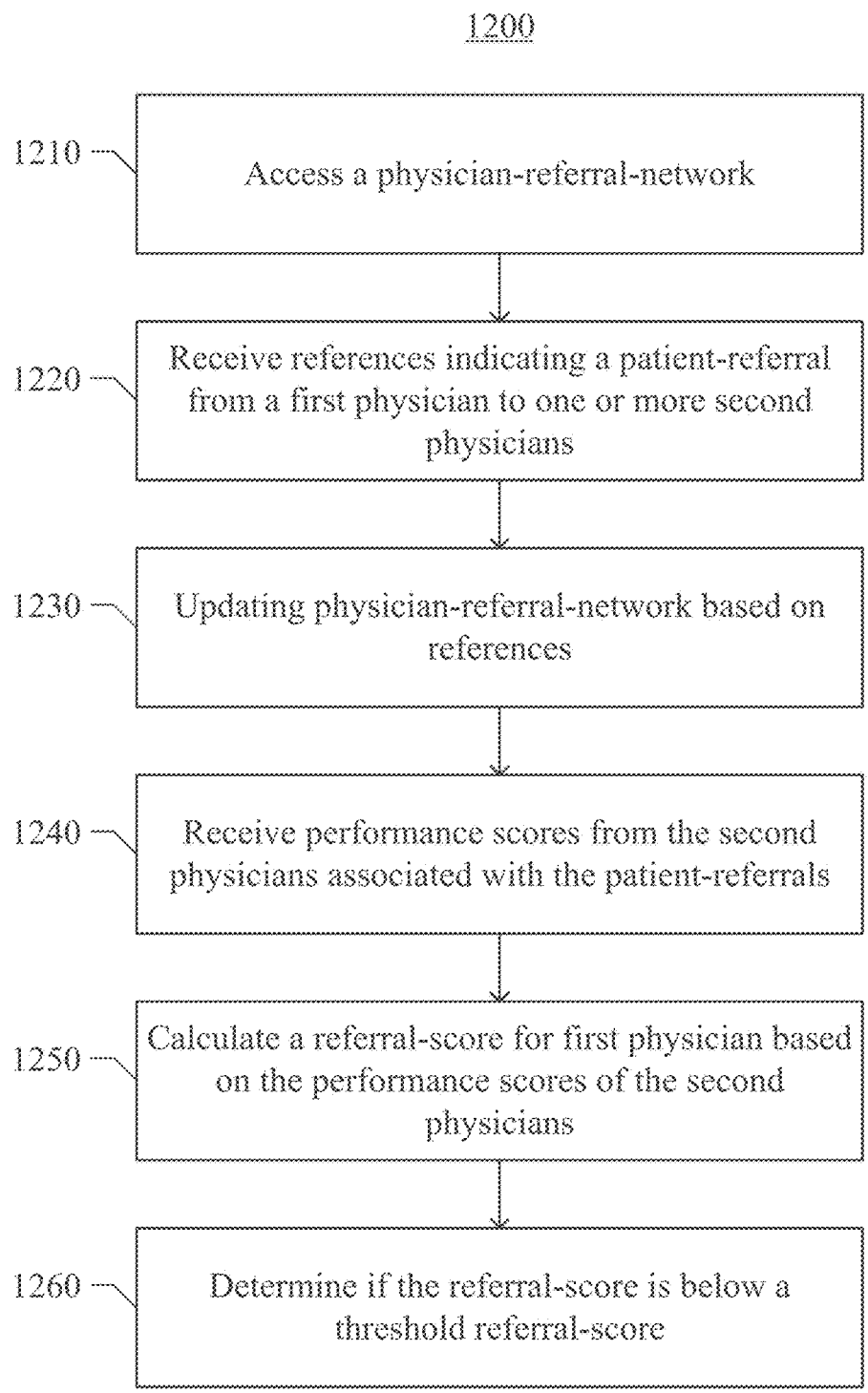
FIG. 12 illustrates an example method of updating a physician-referral-network.

FIG. 12 illustrates an example method for maintaining a record of patient referrals between physicians in a physician-referral-network. At step 1210, a physician-referral-network may be accessed by matching-engine system 160. At step 1220, matching-engine system 160 may receive a reference indicating a patient referral from a first physician to one or more second physicians. At step 1230, matching-engine system 160 may update the physician-referral-network based on the received reference. In particular embodiments, matching-engine system 160 may create a new edge connecting the nodes corresponding to the first physician and the second physicians. As an example and not by way of limitation, the first physician may be referring a patient to the second physician for the first time. In particular embodiments, an edge may already exist between the first physician and the second physicians. In this case, matching-engine system 160 may update the physician-referral-network to indicate that another referral has been made from the first physician to the second physician. At step 1240, matching-engine system 160 may receive performance scores from the second physicians, wherein the performance scores correspond to the patients referred to the second physicians by the first physician.

At step 1250, matching-engine system 160 may calculate a referral-score based at least in part on the received performance scores. In particular embodiments, the referral-score may be calculated by determining an average performance score for all the referrals from the first physician to the second physician. In particular embodiments, the average may be weighted based on the time of the referral, wherein recent referrals receive a higher weight than older referrals. In particular embodiments, the referral-score may be further based on the experience index of the second physicians, compared to a threshold experience index. In particular embodiments, the threshold experience index may be the average experience index of other physicians referred to by the first physician. In particular embodiments, the threshold experience index may be the average experience index of other physicians referred to by the first physician's peer group for similar conditions or treatments. At step 1260, matching-engine system 160 may determine if the referral-score is below a threshold referral-score. The threshold referral-score may be specified by an administrator or another user of matching-engine system 160, or may be determined by matching-engine system 160. As an example and not by way of limitation, the threshold referral-score may be the bottom 5% of all referral scores. If a particular referral-score is below the threshold, matching-engine system 160 may take further action, such as informing the first physician or the second physician, or by removing the first physician from the set of recommended physicians for one or more conditions or treatments.

Particular embodiments may repeat one or more steps of the method of FIG. 12, where appropriate. Although this disclosure describes and illustrates particular steps of the method of FIG. 12 as occurring in a particular order, this disclosure contemplates any suitable steps of the method of FIG. 12 occurring in any suitable order. Moreover, although this disclosure describes and illustrates particular components, devices, or systems carrying out particular steps of the method of FIG. 12, this disclosure contemplates any suitable combination of any suitable components, devices, or systems carrying out any suitable steps of the method of FIG. 12.

In particular embodiments, matching-engine system 160 may consider additional degrees of referrals made by physicians in calculating a referral-score. As an example and not by way of limitation, physician Dr. Grant may refer his patients with migraines to Dr. Sattler. Dr. Sattler may in turn refer some of those patients further to Dr. Malcolm. Matching-engine system 160 may calculate a referral-score for Dr. Sattler based on her referrals to Dr. Malcolm and any performance scores received as a result; additionally, Dr. Malcolm's performance scores or Dr. Sattler's referral-score for Dr. Malcolm for the migraine patients may be used as a factor in calculating the referral-score for Dr. Grant, the original referring physician. In particular embodiments, low performance scores by Dr. Malcolm with respect to Dr. Sattler may be reflected in Dr. Sattler's performance scores with respect to Dr. Grant. In particular embodiments, the additional step of performance scores and referral-scores may mask any inefficiencies at the end of the referral chain. As an example and not by way of limitation, Dr. Sattler may be extremely resource-efficient in her work, such that any inefficiencies from Dr. Malcolm do not carry through to any performance scores or referral-score from Dr. Grant's point of view. Therefore, it may be desirable for matching-engine system 160 to determine separately for Dr. Grant if any physician in a referral chain is inefficient. In particular embodiments, matching-engine system 160 may inform Dr. Grant that his referrals to Dr. Sattler result in inefficiencies further down the line.

Example Search

Figure 13:
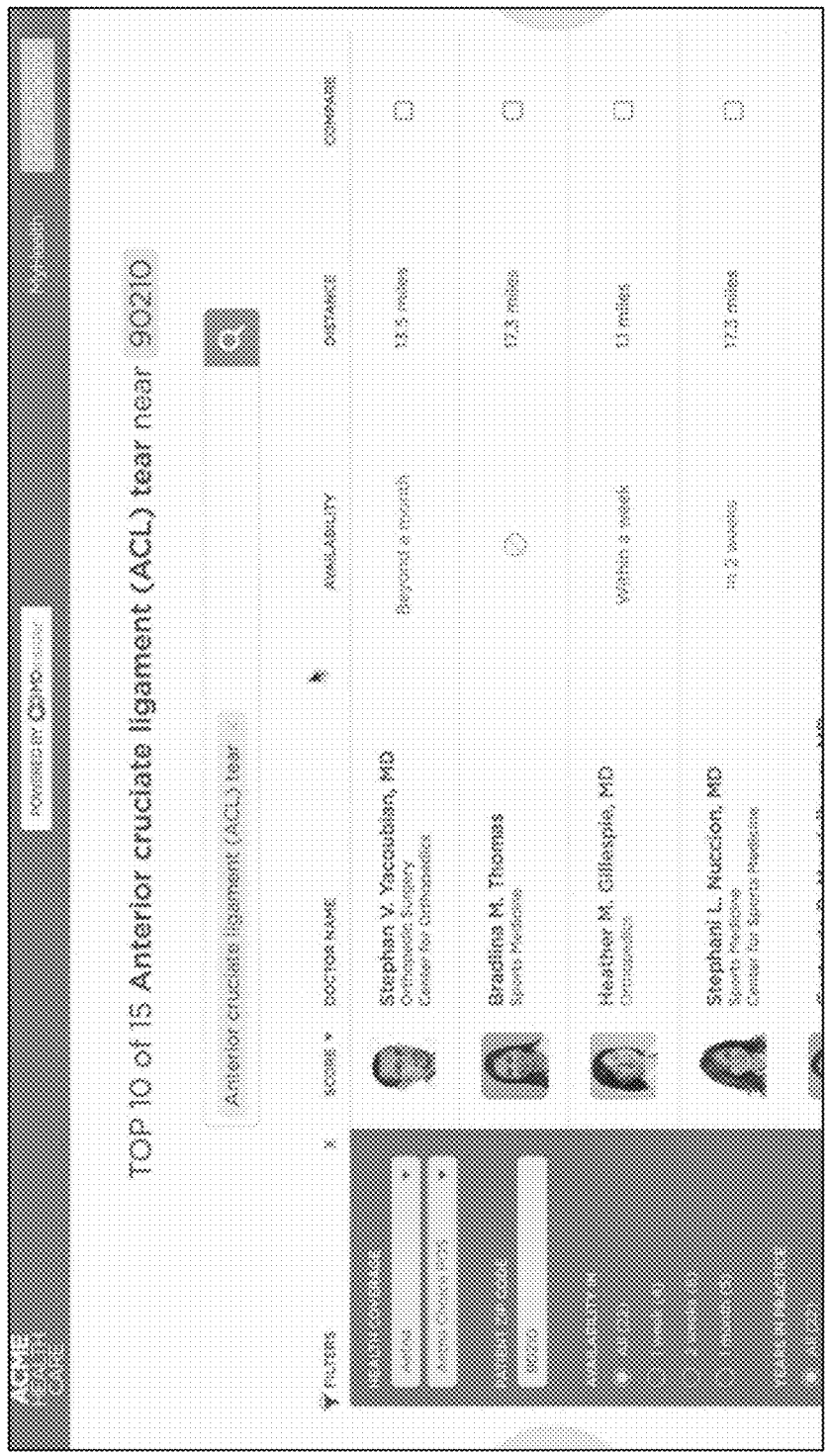
FIG. 13 illustrates an example web interface showing a search results list of physicians corresponding to an entered search query.

FIG. 13 illustrates an example user interface for a search query for a physician. In the example of FIG. 13, a user may have input a search for "Anterior cruciate ligament (ACL) tear." In this example user interface, the user may be presented with a number of physicians that have a high score for the base concept of ACL tear, along with relevant information for each physician. Relevant information may include the general availability of the physician, such as the physician's next availability, and their distance to a location of the searching user.

Figure 14:
FIG. 14 illustrates an example web interface to find a physician for a particular medical specialty, condition, procedure, or under a particular name.

FIG. 14 illustrates an example user interface for a search query for a physician. In the example of FIG. 14, a user may have entered a search for "Clinical Cardiac Electrophysiology." Matching-engine system 160 may present a set of physicians who are relevant to the base concept for cardiac electrophysiology. In the example of FIG. 14, the user interface may provide additional relevant information for each physician, including a matching score for the physician, a number of previous procedures in the base concept in the last time period that each physician had performed, availability, and distance.

Figure 15:
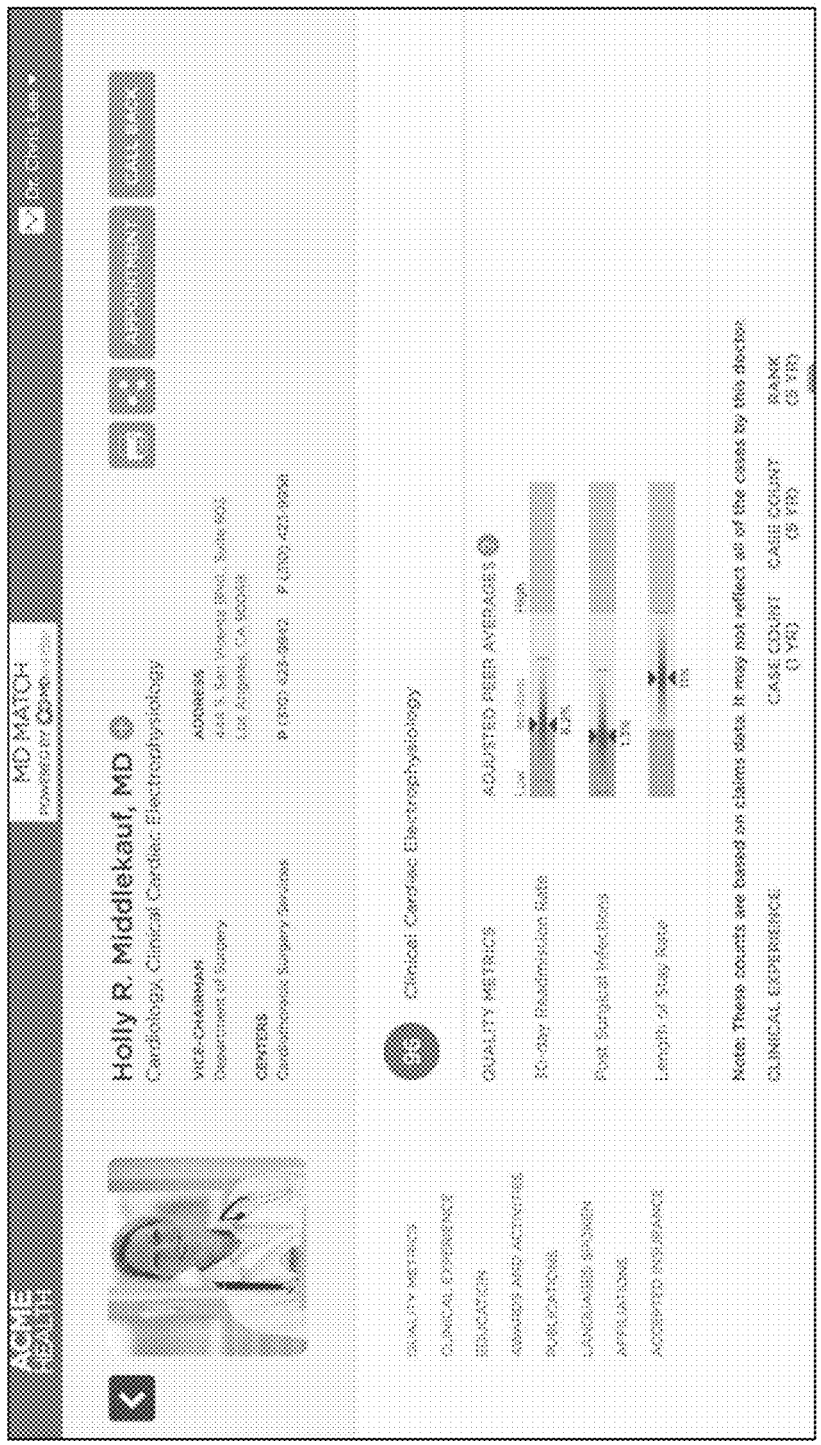
FIG. 15 illustrates an example web interface describing metrics associated with a particular healthcare provider.

FIG. 15 illustrates an example user interface displaying information about a particular physician for the search from FIG. 14. For a particular physician, the user interface may include additional details, such as a 30-day readmission rate, rate of post-surgical infections, and a length of stay rate for the physician. In particular embodiments, these factors may be components of the overall score awarded to the particular physician.

Figure 16:
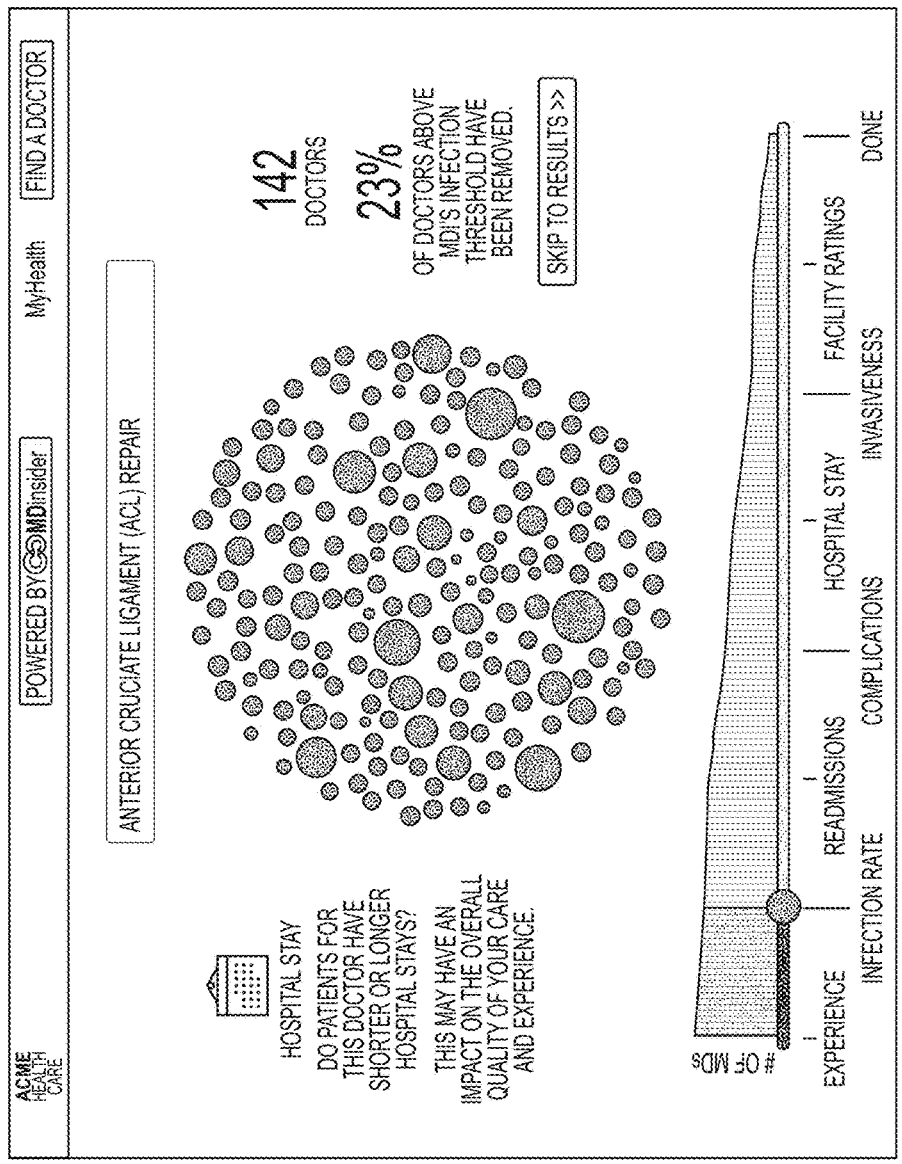
FIG. 16 illustrates an example web interface describing a filtering step used to filter a set of physicians matching an entered search query.

FIG. 16 illustrates an example user interface displaying a step of filtering a set of physicians who are experienced for a particular base concept. In the example of FIG. 16, the base concept entered by the user may be ACL repair. In this example, a number of doctors may have been filtered out based on an infection threshold rate. The set of physicians may have been further filtered based on a length of hospital stays for the physician.

Figure 17:
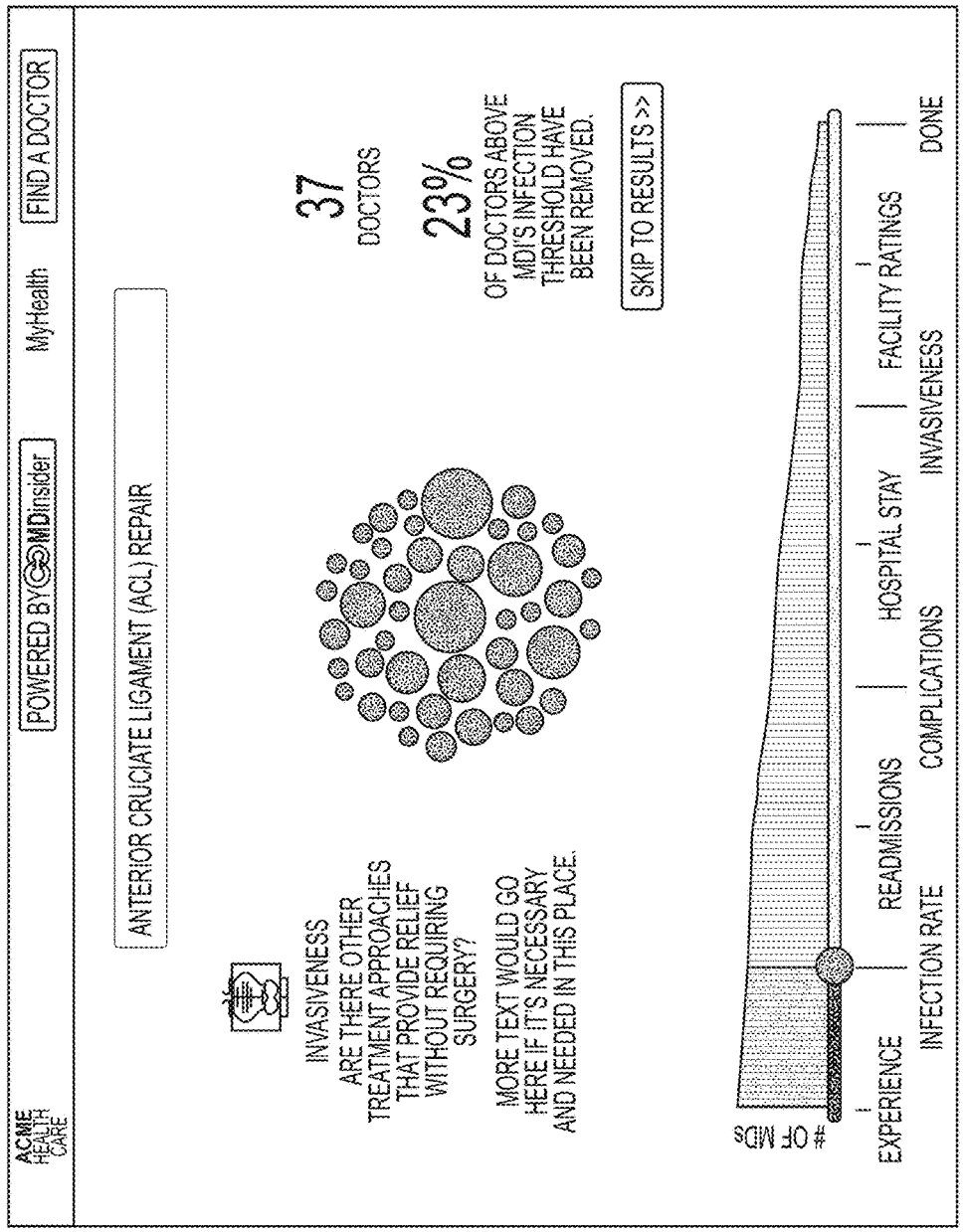
FIG. 17 illustrates an example web interface describing a filtering step used to filter a set of physicians matching an entered search query.

FIG. 17 illustrates an example user interface displaying a step of filtering the set of physicians from FIG. 16 further based on the invasiveness of the physician's procedures. In the example of FIG. 17, the set of physicians may have been filtered to a set of 37 physicians.

Figure 18:
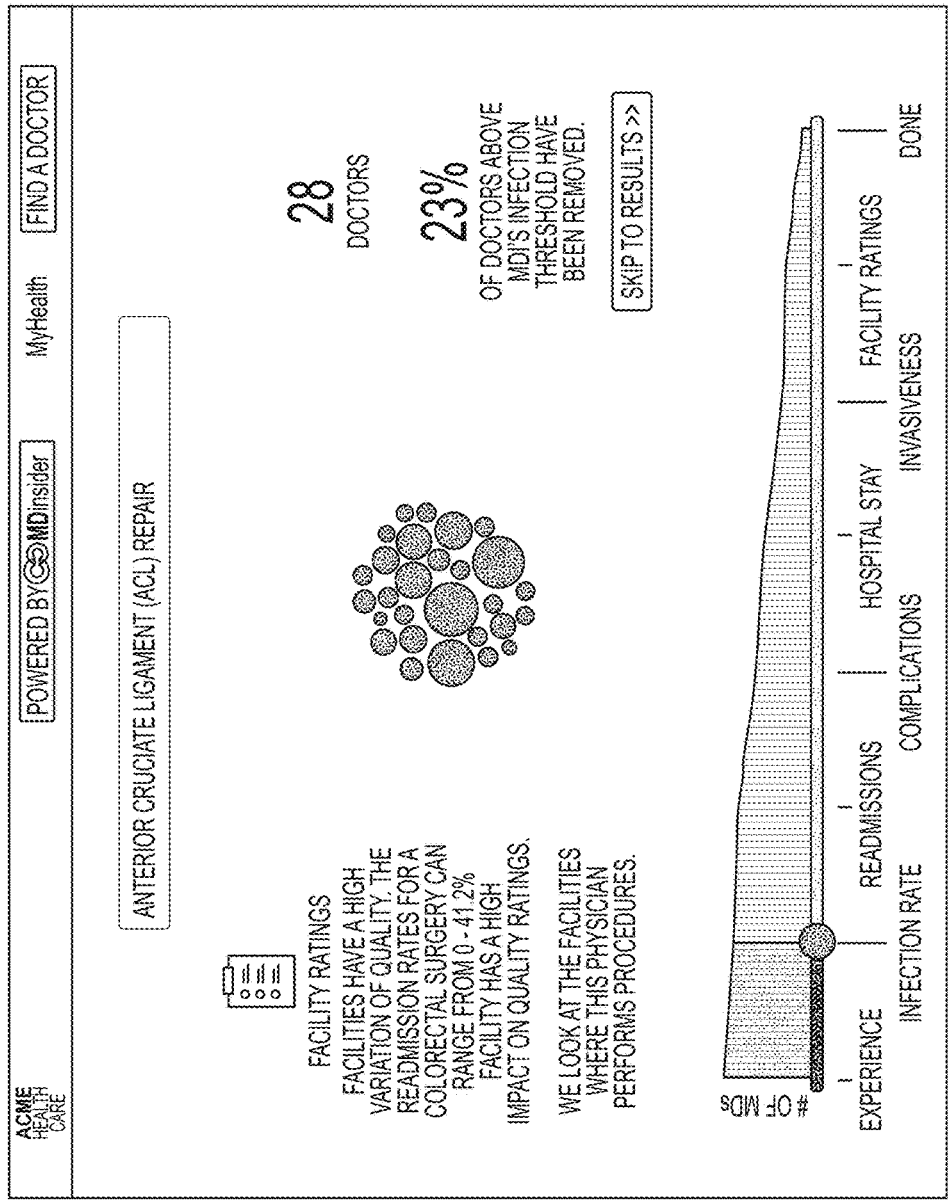
FIG. 18 illustrates an example web interface describing a filtering step used to filter a set of physicians matching an entered search query.

FIG. 18 illustrates an example user interface displaying a step of filtering the set of physicians from FIG. 17 further based on a facility rating for the physician. The facility rating may reflect the quality of the facility which could affect other factors such as readmission rates. In the example of FIG. 18, the set of physicians may have been filtered to 28 physicians.

Privacy

In particular embodiments, one or more of the data objects of the online healthcare provider search engine may be associated with a privacy setting. The privacy settings (or "access settings") for an object may be stored in any suitable manner, such as, for example, in association with the object, in an index on an authorization server, in another suitable manner, or any combination thereof. A privacy setting of an object may specify how the object (or particular information associated with an object) can be accessed (e.g., viewed or shared) using the online healthcare provider search engine. Where the privacy settings for an object allow a particular user to access that object, the object may be described as being "visible" with respect to that user. As an example and not by way of limitation, a user of the online healthcare provider search engine may specify privacy settings for a user-profile page identify a set of users that may access the work experience information on the user-profile page, thus excluding other users from accessing the information. In particular embodiments, the privacy settings may specify a "blocked list" of users that should not be allowed to access certain information associated with the object. In other words, the blocked list may specify one or more users or entities for which an object is not visible. As an example and not by way of limitation, a user may specify a set of users that may not access photos albums associated with the user, thus excluding those users from accessing the photo albums (while also possibly allowing certain users not within the set of users to access the photo albums). In particular embodiments, privacy settings may be associated with particular patient information. Privacy settings may specify how one or more items of patient information can be accessed using the online healthcare provider search engine. In particular embodiments, privacy settings may allow users to opt in or opt out of having their actions logged by matching-engine system 160 or shared with other systems (e.g., third-party system 170). In particular embodiments, the privacy settings associated with an object may specify any suitable granularity of permitted access or denial of access. As an example and not by way of limitation, access or denial of access may be specified for particular users, user groups, user networks, all users ("public"), no users ("private"), users of third-party systems 170, particular applications (e.g., third-party applications, external websites), other suitable users or entities, or any combination thereof. Although this disclosure describes using particular privacy settings in a particular manner, this disclosure contemplates using any suitable privacy settings in any suitable manner.

In particular embodiments, one or more servers 162 may be authorization/privacy servers for enforcing privacy settings. In response to a request from a user (or other entity) for a particular object stored in a data store 164, matching-engine system 160 may send a request to the data store 164 for the object. The request may identify the user associated with the request and may only be sent to the user (or a client system 130 of the user) if the authorization server determines that the user is authorized to access the object based on the privacy settings associated with the object. If the requesting user is not authorized to access the object, the authorization server may prevent the requested object from being retrieved from the data store 164, or may prevent the requested object from be sent to the user. Although this disclosure describes enforcing privacy settings in a particular manner, this disclosure contemplates enforcing privacy settings in any suitable manner.

Miscellaneous

Herein, "or" is inclusive and not exclusive, unless expressly indicated otherwise or indicated otherwise by context. Therefore, herein, "A or B" means "A, B, or both," unless expressly indicated otherwise or indicated otherwise by context. Moreover, "and" is both joint and several, unless expressly indicated otherwise or indicated otherwise by context. Therefore, herein, "A and B" means "A and B, jointly or severally," unless expressly indicated otherwise or indicated otherwise by context.

The scope of this disclosure encompasses all changes, substitutions, variations, alterations, and modifications to the example embodiments described or illustrated herein that a person having ordinary skill in the art would comprehend. The scope of this disclosure is not limited to the example embodiments described or illustrated herein. Moreover, although this disclosure describes and illustrates respective embodiments herein as including particular components, elements, functions, operations, or steps, any of these embodiments may include any combination or permutation of any of the components, elements, functions, operations, or steps described or illustrated anywhere herein that a person having ordinary skill in the art would comprehend. Furthermore, reference in the appended claims to an apparatus or system or a component of an apparatus or system being adapted to, arranged to, capable of, configured to, enabled to, operable to, or operative to perform a particular function encompasses that apparatus, system, component, whether or not it or that particular function is activated, turned on, or unlocked, as long as that apparatus, system, or component is so adapted, arranged, capable, configured, enabled, operable, or operative.

What is claimed is:

1. A method comprising:
    receiving, by one or more computing devices of a matching-engine system, a search query from a client device of a user of the matching-engine system, the search query comprising:
        a geographic location of the user;
        a preferred date and time for an appointment for the user; and
        one or more of a user-specified symptom or a user-specified treatment;
    determining, by one or more of the computing devices, at least one base-concept based on the search query, the base-concept comprising a medical diagnosis or a medical procedure;
    identifying, by one or more of the computing devices, a set of one or more physicians to be recommended to the user based at least in part on:
        a geographic location of each of the one or more physicians;
        an availability of each of the one or more physicians with respect to the preferred date and time for the appointment for the user;
        a performance-score of each of the one or more physicians associated with the base-concept, wherein the performance-score is calculated based on a weighted aggregate of individual performance-scores for one or more sub-concepts of the base-concept, wherein the individual performance-scores are calculated by:
(1) accessing one or more Current Procedural Terminology (CPT) codes based on claims data received from the physician, wherein the CPT codes refer to a medical service provided by the physician in connection with the one or more sub-concepts;
(2) determining one or more relative value units (RVUs) corresponding to the one or more CPT codes, wherein the RVUs corresponding to a CPT code represents a location-independent measure of overall resources used for the medical service;
(3) calculating a physician-cost-factor for the physician associated with the one or more sub-concepts, wherein the physician-cost-factor is based on the RVUs corresponding to the medical service provided by the physician for the one or more sub-concepts;
(4) accessing an average cost factor associated with the one or more sub-concepts for a plurality of physicians, wherein the physician and the plurality of physicians share a common specialty and common geographic location; and
(5) comparing the physician-cost-factor with the average cost factor, wherein the individual performance-score for the physician for the one or more sub-concepts is increased if the physician-cost-factor is lower than the average cost factor;
a readmission rate of each of the one or more physicians;
a reinfection rate of each of the one or more physicians;
an average length-of-stay for patients of each of the one or more physicians;
a relative invasiveness of procedures of each of the one or more physicians; and
a rating of a healthcare facility associated with each of the one or more physicians; and
sending, by one or more computing devices, a search-results page to a client device of the user, the search-results page comprising references to one or more of the physicians in the set of physicians.

2. The method of claim 1, wherein the readmission rate for a particular physician is a rate at which patients treated by the particular physician are readmitted to a healthcare facility within a particular period of time of receiving treatment from the particular physician.

3. The method of claim 1, wherein the average length-of-stay for a particular physician comprises an average amount of time of the length-of-stay in a healthcare facility for patients seen by the particular physician for the base-concept.

4. The method of claim 1, wherein the reinfection rate for a particular physician comprises a rate at which patients treated by the particular physician are diagnosed with an infection or other post-treatment complications within a particular period of time of receiving treatment from the particular physician.

5. The method of claim 1, wherein the relative invasiveness of procedures for a particular physician is based on an invasiveness value associated with treatments performed by the particular physician within a particular period of time.

6. The method of claim 1, wherein identifying the set of one or more physicians is further based on a score associated with each physician, and a higher rating for the healthcare facility associated with a particular physician increases the score for the particular physician.

7. The method of claim 1, wherein each physician in the set is associated with:
a performance-score associated with the base-concept within a range of acceptable performance-scores; and
an experience-score associated with the base-concept within a range of acceptable experience-scores.

8. The method of claim 7, wherein the experience-score is based at least in part on a volume of cases seen by the physician, a severity associated with each case seen by the physician, and a variety of cases seen by the physician.

9. The method of claim 8, wherein the volume of cases and the variety of cases comprises cases in a condition group common to a condition group associated with the base-concept.

10. The method of claim 7, wherein the set of one or more physicians is ranked for presentation based at least in part on the performance-score and experience-score of each physician.

11. The method of claim 7, wherein the experience-score is determined by an experience-engine of the matching-engine system based at least in part on one or more International Classification of Diseases (ICD) codes received from a physician or health-care provider, wherein each ICD code corresponds to a medical diagnosis associated with a patient.

12. The method of claim 1, wherein the common geographic location comprises:
a metropolitan statistical area; or
a geographic location defined by the user.

13. The method of claim 1, wherein the cost factors comprise a monetary cost for treating the base-concept.

14. The method of claim 1, wherein the cost factors comprise one or more relative value units (RVU) corresponding to one or more procedure codes associated with the base-concept.

15. The method of claim 1, wherein the performance-score is further based on one or more sub-concepts associated with the base-concept, the sub-concept being determined by a user history or user input of additional user-specified symptoms or user-specified treatments.

16. The method of claim 1, wherein the determining the base-concept is based on user input of the user-specified treatment or user-specified symptoms, and a clinical taxonomy for translating the user input to a defined base-concept.

17. One or more computer-readable non-transitory storage media embodying software that is operable when executed to:
receive a search query from a client device of a user of the matching-engine system, the search query comprising:
a geographic location of the user;
a preferred date and time for an appointment for the user; and
one or more of a user-specified symptom or a user-specified treatment;
determine at least one base-concept based on the search query, the base-concept comprising a medical diagnosis or a medical procedure;
identify a set of one or more physicians to be recommended to the user based at least in part on:
a geographic location of each of the one or more physicians;
an availability of each of the one or more physicians with respect to the preferred date and time for the appointment for the user;
a performance-score of each of the one or more physicians associated with the base-concept, wherein the performance-score is calculated based on a weighted aggregate of individual performance-scores for one or more sub-concepts of the base-concept, wherein the individual performance-scores are calculated by:
(1) accessing one or more Current Procedural Terminology (CPT) codes based on claims data received from the physician, wherein the CPT codes refer to a medical service provided by the physician in connection with the one or more sub-concepts;
(2) determining one or more relative value units (RVUs) corresponding to the one or more CPT codes, wherein the RVUs corresponding to a CPT code represents a location-independent measure of overall resources used for the medical service;
(3) calculating a physician-cost-factor for the physician associated with the one or more sub-concepts, wherein the physician-cost-factor is based on the RVUs corresponding to the medical service provided by the physician for the one or more sub-concepts;
(4) accessing an average cost factor associated with the one or more sub-concepts for a plurality of physicians, wherein the physician and the plurality of physicians share a common specialty and common geographic location; and
(5) comparing the physician-cost-factor with the average cost factor, wherein the individual performance-score for the physician for the one or more sub-concepts is increased if the physician-cost-factor is lower than the average cost factor;
a readmission rate of each of the one or more physicians;
a reinfection rate of each of the one or more physicians;
an average length-of-stay for patients of each of the one or more physicians;
a relative invasiveness of procedures of each of the one or more physicians; and
a rating of a healthcare facility associated with each of the one or more physicians; and
send a search-results page to a client device of the user, the search-results page comprising references to one or more of the physicians in the set of physicians.

18. A system comprising:
one or more processors; and
a memory coupled to the processors comprising instructions executable by the processors, the processors being operable when executing the instructions to:
  receive a search query from a client device of a user of the matching-engine system, the search query comprising:
    a geographic location of the user;
    a preferred date and time for an appointment for the user; and
    one or more of a user-specified symptom or a user-specified treatment;
  determine at least one base-concept based on the search query, the base-concept comprising a medical diagnosis or a medical procedure;
  identify a set of one or more physicians to be recommended to the user based at least in part on:
    a geographic location of each of the one or more physicians;
    an availability of each of the one or more physicians with respect to the preferred date and time for the appointment for the user;
    a performance-score of each of the one or more physicians associated with the base-concept, wherein the performance-score is calculated based on a weighted aggregate of individual performance-scores for one or more sub-concepts of the base-concept, wherein the individual performance-scores are calculated by:
      (1) accessing one or more Current Procedural Terminology (CPT) codes based on claims data received from the physician, wherein the CPT codes refer to a medical service provided by the physician in connection with the one or more sub-concepts;
      (2) determining one or more relative value units (RVUs) corresponding to the one or more CPT codes, wherein the RVUs corresponding to a CPT code represents a location-independent measure of overall resources used for the medical service;
      (3) calculating a physician-cost-factor for the physician associated with the one or more sub-concepts, wherein the physician-cost-factor is based on the RVUs corresponding to the medical service provided by the physician for the one or more sub-concepts;
      (4) accessing an average cost factor associated with the one or more sub-concepts for a plurality of physicians, wherein the physician and the plurality of physicians share a common specialty and common geographic location; and
      (5) comparing the physician-cost-factor with the average cost factor, wherein the individual performance-score for the physician for the one or more sub-concepts is increased if the physician-cost-factor is lower than the average cost factor;
    a readmission rate of each of the one or more physicians;
    a reinfection rate of each of the one or more physicians;
    an average length-of-stay for patients of each of the one or more physicians;
    a relative invasiveness of procedures of each of the one or more physicians; and
    a rating of a healthcare facility associated with each of the one or more physicians; and
  send a search-results page to a client device of the user, the search-results page comprising references to one or more of the physicians in the set of physicians.

* * * * *